United States Patent [19]
Frankel

[11] Patent Number: 6,096,496
[45] Date of Patent: Aug. 1, 2000

[54] SUPPORTS INCORPORATING VERTICAL CAVITY EMITTING LASERS AND TRACKING APPARATUS FOR USE IN COMBINATORIAL SYNTHESIS

[76] Inventor: Robert D. Frankel, 285 Idlewood Rd., Rochester, N.Y. 14618

[21] Appl. No.: 08/879,298

[22] Filed: Jun. 19, 1997

[51] Int. Cl.[7] .......................... C12Q 1/00; G01N 35/53; G01N 21/00; G11C 11/00
[52] U.S. Cl. .................................. 435/4; 435/6; 435/7.1; 435/DIG. 41; 435/DIG. 45; 436/501; 436/518; 422/55; 365/129; 365/151; 365/155
[58] Field of Search .................... 435/4, 6, 7.1, DIG. 45, 435/DIG. 41; 436/518, 501; 365/129, 174, 151, 153; 422/55

[56] References Cited

U.S. PATENT DOCUMENTS

| | | |
|---|---|---|
| 4,539,507 | 9/1985 | VanSlyke et al. . |
| 4,833,092 | 5/1989 | Geysen . |
| 5,034,613 | 7/1991 | Denk et al. . |
| 5,136,572 | 8/1992 | Bradley . |
| 5,141,671 | 8/1992 | Bryan et al. . |
| 5,214,409 | 5/1993 | Beigel . |
| 5,252,962 | 10/1993 | Urbas et al. . |
| 5,257,011 | 10/1993 | Beigel . |
| 5,266,926 | 11/1993 | Beigel . |
| 5,351,052 | 9/1994 | D'Hont et al. . |
| 5,405,709 | 4/1995 | Littman et al. . |
| 5,409,783 | 4/1995 | Tang et al. . |
| 5,438,878 | 8/1995 | Carroll, Jr. . |
| 5,448,582 | 9/1995 | Lawandy . |
| 5,558,904 | 9/1996 | Hsieh et al. . |
| 5,565,324 | 10/1996 | Still et al. . |
| 5,641,634 | 6/1997 | Mandecki ................................ 435/6 |
| 5,751,629 | 5/1998 | Nova et al. ........................... 365/151 |
| 5,770,455 | 6/1998 | Cargill et al. ........................ 436/518 |

FOREIGN PATENT DOCUMENTS

| | | |
|---|---|---|
| 9636436 | 11/1996 | WIPO . |
| 9808077 | 3/1998 | WIPO . |

OTHER PUBLICATIONS

Optics & Filters, Oriel Corporation, vol. III.
Fumitomo Hide, Maria A. Diaz–Garcia, and Alan J. Heeger, Luminescent Polymers Promise Novel Lasers, Laser Focus World, May 1997, pp. 151–156.
R.M. Balachandran, D.P. Pacheco, and N.M. Lawandy, Laser Action in Polymeric Gain Media Containing Scattering Particles, Applied Optics, vol. 35, No. 4, Feb. 1, 1996, pp. 640–643.
N.E.J. Hunt, E.F. Schubert, R.A. Logan, and G.J. Zydzik, Enhanced Spectral Power Density and Reduced Linewidth at $1.3\mu m$ in an INGAAsP Quantum Well Resonant–Cavity Light–Emitting Diode, Appl. Phys. Lett. 61 (19), Nov. 9, 1992, American Institute of Physics, pp. 2287–2289.
J.A. Lott, R.P. Schneider, Jun., G.A. Vawter, J.C. Zolper and K.J. Malloy, Visible (660 nm) Resonant Cavity Light–Emitting Diodes, Electronics Letters, Feb. 18, 1993, vol. 29, No. 4, pp. 328–329.
Sydney Brenner and Richard A. Lerner, Encoded Combinatorial Chemistry, Proc. Natl. Acad. Sci. USA, vol. 89, Jun. 1992, pp. 5381–5383.
Fumitomo Hide, Maria A. Diaz–Garcia, Benjamin J. Schwartz, Mats R. Andersson, Qibing Pei, Alan J. Heeger, Semiconducting Polymers: A New Class of Solid–State Laser Materials, Science, vol. 273, Sep. 27, 1996, pp. 1833–1837.

(List continued on next page.)

*Primary Examiner*—Donald E. Adams
*Assistant Examiner*—Joseph W. Ricigliano
*Attorney, Agent, or Firm*—Wall Marjama Bilinski & Burr

[57] ABSTRACT

A combinatorial chemistry bead that includes an electromagnetic spectral emitter that radiates a distinct electromagnetic code for each bead that uniquely identifies each bead, a terminal apparatus for receiving the electromagnetic code from each bead, and a method for performing combinatorial synthesis using a bead that transmits a distinct electromagnetic code. The invention includes a large number of spectrally narrowed light emitting mechanisms for generating distinct optical codes.

12 Claims, 12 Drawing Sheets

OTHER PUBLICATIONS

Stephen P.A. Fodor, J. Leighton Read, Michael C. Pirrung, Lubert Stryer, Amy Tsai Lu, Dennis Solas, Light–directed, Spatially Addressable Parallel Chemical Synthesis, Research Article, Science, vol. 251, Feb. 15, 1991, pp. 767–773.

Anthony Yen, Erik H. Anderson, R.A. Ghanbari, M.L. Schattenburg, and Henry I. Smith, Achromatic Holographic Configuration For 100–nm–period Lithography, Applied Optics, vol. 31, No. 22, Aug. 1, 1992, pp. 4540–4544.

H.B. Lon and A.J. Campillo, New Nonlinear Optics in Droplet Microcavities Displaying Enhanced Gain, Physical Review Letters, vol. 73, No. 18, Oct. 31, 1994 The American Physical Society, pp. 2440–2443.

Nabil M. Lawandy, 'Paint–On Lasers' Light the Way for New Technologies, Photonics Spectra, Jul. 1994, pp. 119–122.

Edmund J. Moran, et al., Radio Frequency Tag Encoded Combinatorial Library Method for the Discovery of Tripeptide–Substituted Cinnamic Acid Inhibitors of the Protein Tyrosine Phosphatase PTPIB, J. Am. Chem. Soc., 1995, 117, 10787–10788.

Process Builds Silicon RF Chips, Electrical Engineering Times, Nov. 25, 1996, pp 37–38.

K.C. Nicolaou, Xiao–Yi Xiao, Zahra Parandoosh, Andrew Senyei, Michael P. Nova, Radiofrequency Encoded Combinatorial Chemistry, Agnew, Chem. Int. Ed. Engl., 1995, 34, No. 20.

J. Grüner, F. Cacialli, and R.H. Friend, Appl. Phys. 80, Jul. 1, 1996, pp. 207–215.

N. Tessler, G.J. Denton & R.H. Friend, Lasing from Conjugated–Polymer Microcavites, Nature, vol. 382, Aug. 22, 1996, pp. 695–697.

A. Dodabalapur, L.J. Rothberg, and T.M. Miller, Color Variation with Electroluminescent Organic Semiconductors in Multimode Resonant Cavities, Appl. Phys. Lett., vol. 65, Oct. 31, 1994, pp 2308–2310.

A. Dodabalapur, L.J. Rothenberg, t.M. Miller and E.W. Kwock, Microcavity Effects in Organic Semiconductors, Appl. Phys. Lett, vol. 64 (19), May 9, 1994, pp. 2486–2488.

C.W. Tang, S.A. VanSlyke, and C.H. Chen, Electroluminescence of Doped Organic Thin Fims, J. Appl. Phys. vol. 65 (9), May 1, 1989, pp. 3610–3616.

S.A. VanSlyke, C.H. Chen and C.W. Tang, Organic Electroluminescent Devices with Improved Stability, Appl. Phys. Lett. vol. 69, No. 15, Oct. 7, 1996, pp. 2160–2162.

C.W. Tang and S.A. VanSlyke, Organic Electroluminescent Diodes, Appl. Phys. Lett., vol. 51, No. 12, Sep. 21, 1987, pp. 913–915.

V. Bulović G. Gu, P.E. Burrows, S.R. Forrest, M. E. Thompson, Transparent Light–Emitting Devices, Nature, vol. 380, Mar. 7, 1996, p. 29.

Michael A. Scobey, Walter J. Lekki and Thomas W. Geyer, Filters Create Thermally Stable, Passive Muliplexers, Laser Focus World, Mar. 1997, pp. 111–116.

H. Yokoyama, Physics and Device Applications of Optical Microcavities, Science, vol. 256, Apr. 3, 1992, pp. 66–70.

S.M. Sze, Physics of Semiconductor Devices, Chapter 13 (1981), pp. 743–789.

S.M. Sze, Solar Cells, Chapter 14 (1981), pp. 790–838.

Charles A. Harper and Harold C. Jones, Active Electronic Component Handbook, Phototonic Components, Chapter 9, pp. 9.52–9.61, (1996).

Charles A. Harper and Harold C. Jones, Active Electronic Component Handbook, Component Parts for Microwave Systems, Chapter5, pp. 5.2–5.21, (1996).

Amnon Yariv, Quantum Electronics, Guided Wave Optics–Propagation on Optical Fibers, Chapter 22, pp. 604–623, (1989).

Amnon Yariv, Quantum Electronics, Third–Order Optical Nonlinearities–Stimulated Raman and Brillouin Scattering, Chapter 18, pp. 453–475, (1989).

M.C. Larson and J.S. Harris, Jr., Broadly–Turnable Resonant–Cavity Light–Emitting Diode, IEEE Photons, Letters, 1995, pp. 1267–1269.

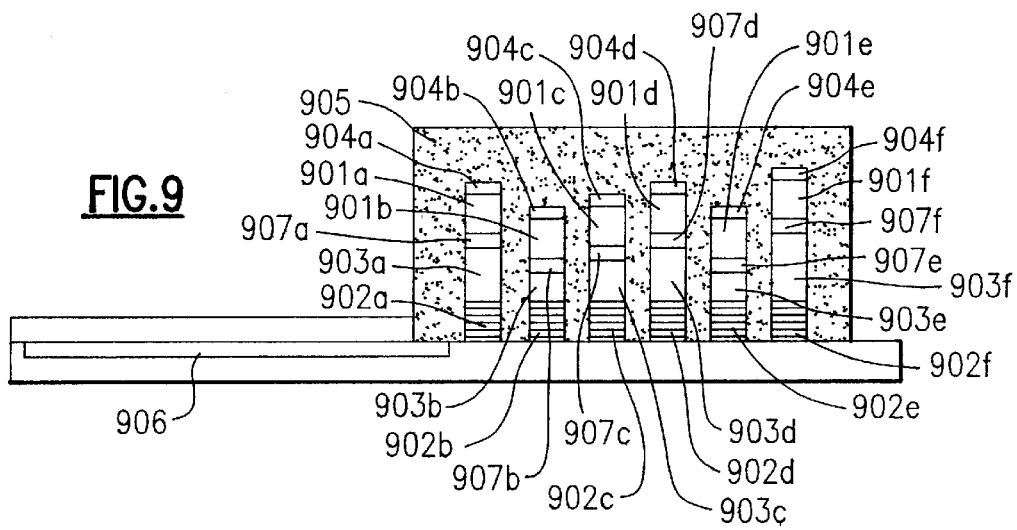
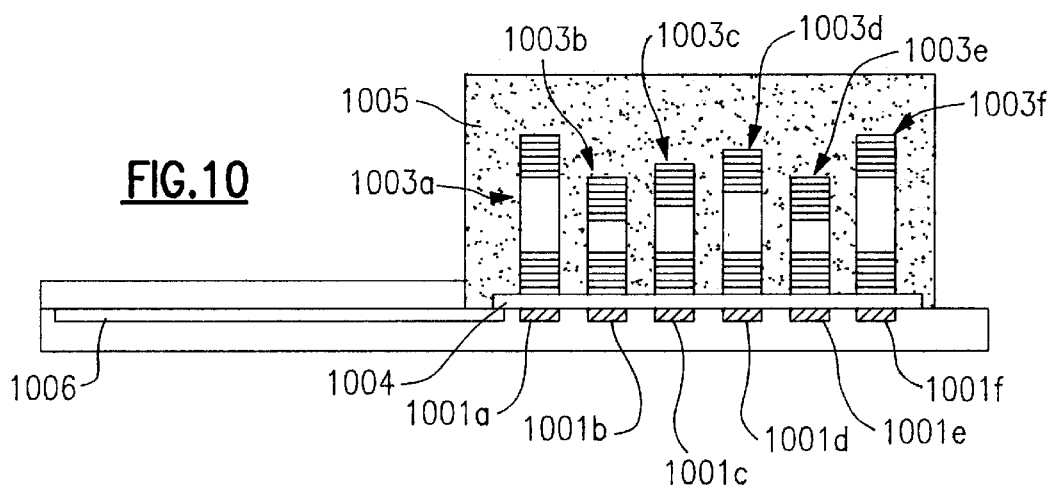
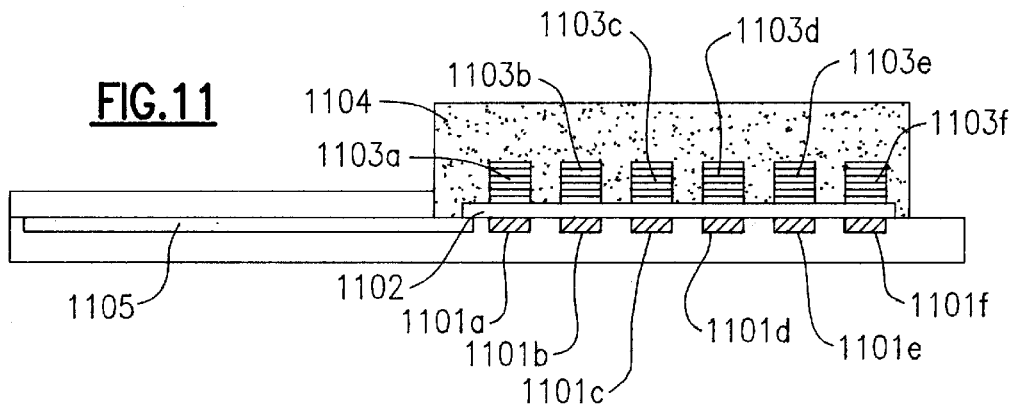

SUPPORTS INCORPORATING VERTICAL CAVITY EMITTING LASERS AND TRACKING APPARATUS FOR USE IN COMBINATORIAL SYNTHESIS

BACKGROUND OF THE INVENTION

The present invention relates to an apparatus and method for use in identifying an oligomeric compound (or molecule) that is synthesized into other chemical compounds, particularly those compounds such as pharmaceuticals and biochemicals, by the techniques of combinatorial chemistry. The identification of the oligomeric is performed by identifying the chemical reaction exposure and assay steps that the oligomeric compound has undergone in its synthesis.

The tracking of the progress of chemical reactions through long sequences of synthesis operations is a matter of ever increasing importance in the development and production of new biochemicals and pharmaceuticals.

One particular example of sequences of reactions of the above described type is known as combinatorial synthesis. Combinatorial synthesis may be defined as the generation of a large and diverse series of compounds by the parallel application of different sequences of synthetic reaction steps, or the addition of different functional chemical groups to a population of previously synthesized molecules. These molecules may be peptides, nucleotides, small organic molecules, etc. These large and diverse series of compounds are referred to as combinatorial libraries. Combinatorial libraries are made by forming all possible combinations of a series of sets of precursor molecules, and applying the same sequence of reactions to each combination. Developments in automation have made it possible to synthesize thousands to billions of distinct compounds in parallel. Early work on processes of this type are described in U.S. Pat. No. 4,833,092 (Geysen), which discusses the parallel synthesis of multiple peptides for use in antibody recognition studies.

Research involving pharmaceuticals and biochemicals is particularly well suited for the use of combinatorial synthesis. An objective of combinatorial synthesis is to create libraries of potential pharmaceutically active compounds. Each of these library compounds can then be examined to determine their binding affinity for a target molecule, where in a pharmaceutical application that binding affinity is characterized as bioactivity. After an assay step in which where there is a binding reaction, the identity or reaction history of a library compound must be determined. This is particularly important because the complex synthesis of biomolecules and potential pharmaceuticals involve a large number of reaction steps.

Furthermore, the techniques described herein can be well utilized in creating libraries for many types of complex molecular syntheses, such as lipids used in detergents, heterocyclic compounds used in fuels, and long chain polymers used in materials. One skilled in the art would recognize that the apparatus and method described herein has utility in identifying each of the compounds in combinatorial libraries that are the products of synthesis reactions used in various areas of commerce.

There are at least three approaches to the determination of these novel compounds: direct structural determination; geometric separation of synthetic and assay steps in defined areas; and identification of the initial oligomeric compound and the chemical reaction sequence that the initial oligomeric compound has undergone by attaching these compounds to tagged beads that record this information by chemical, physical, or electronic; or alternatively transmit a distinct identification (ID) code for each bead. Beads of this type are ordinarily used in large numbers that are processed simultaneously in the same reaction vessel. During a series of synthetic steps, these beads are combined, separated and recombined in new combinations as they pass through a series of reaction vessels to produce a number of different end products simultaneously.

Direct structural determination is often not desirable, because each different molecule is often synthesized in quantities too small for structural determination via standard techniques such as nuclear magnetic resonance spectroscopy, mass spectroscopy or chromatographic fragment identification.

Geometric separation of synthetic and assay steps is exemplified by a chip developed by Fodor et al., and described in Science 251, p. 767 (1991). These investigators developed a process to perform a photochemical linkage of peptides and nucleotides on a planar substrate. Different molecules are made in checkerboard pattern on a board. Assay of receptor binding occurs in place on the board. However, this device is not generally applicable to the standard steps used to synthesize organic pharmaceuticals, many of which are not light driven.

The third identification approach in combinatorial synthesis is to tag small beads. Each tagged bead either includes an identification code distinct from each of the other beads, or includes a recording apparatus that records the sequence of reaction it undergoes during the combinatorial process. The tracking process includes a terminal apparatus that examines the beads and determines information about the chemical reactions to which each bead has been exposed. When this information is analyzed, the reaction history of a complex of series of reactions is determinable. Combinatorial bead libraries comprise combinatorial libraries wherein the generated compounds are attached to beads. Combinatorial chemical bead libraries for drug discovery applications comprise $10^2$–$10^6$ beads. Future libraries may be substantially larger. Thus, a requirement of a bead identification method is high information readout rate.

In most combinatorial synthetic systems that have been implemented to date, information about each synthetic step that the bead has been, or is to be exposed to, is encoded in the bead either prior to placement in a reaction vessel where a particular synthetic step is to be carried out, in the reaction vessel, or after removal from the reaction vessel, and before subsequent placement in a next reaction vessel. At the completion of a given synthetic protocol, chemicals synthesized on the beads are assayed. Information encoded in those beads whose attached synthesized chemicals perform well in the assay is decoded. That information provides the reaction history of each particular bead to enable replication of its attached chemical.

An alternative tagging approach is to tag beads physically with a distinct identification number or code that is predetermined (permanent) during the reaction process. Read out of the bead identification number or code is accomplished by electrical or alternatively electromagnetic radiation transmission. In this approach, each bead is interrogated as to its identification number or code and location prior to, during, and/or after each synthetic reaction, and that information is recorded. That interrogation and recording is accomplished by means of a terminal apparatus computing device because the high readout rate requirement imposed by a relatively large number of beads and a relatively brief available read out time. At the completion of a given synthetic protocol, chemicals synthesized on those beads are assayed. Tag identification of beads on which the chemicals that perform well in the assay are is then determined, and the bead is uniquely identified and correlated with the stored reaction step information to provide the reaction history of each bead, and thus enable replication of the attached oligomeric compound.

There are many possible tagging systems. Beads may be tagged chemically or electronically during the course of a combinatorial synthesis, and alternatively may be tagged with a predetermined (or permanent) electrical, electromagnetic, or physical Identification number or code.

Chemical tags have been implemented by multiple groups and companies. In these protocols, distinct chemical moieties that represent, or code for each step in the synthetic process are added to the bead. After each synthetic and labeling step, the beads are combined, resorted, and a new step in the process is performed. At the end of the process, after the binding assay, beads that have successfully bound the target molecule are separated. The chemical tag is then decoded. This approach is exemplified by the approach of Brenner and Lerner, Proc. Natl. Acad. Sci., U.S.A., 89, pp. 5381–5383 (1992), where the theoretical synthesis of oligonucleotides is used to code for the sequential addition of amino acids to growing peptide chains. This approach is advantageous because the art of oligonucleotide synthesis is well established. This approach suffers, however, from the fact that decoding of the tag requires a slow and complex multi-step procedure and the fact that not all of the original synthetic steps are compatible with the stability of the nucleotide bond.

Another approach to chemical tagging is that described in previously cited U.S. Pat. No. 5,565,324 (Still et al.) used extensively by Pharmacopeia, Inc., in their combinatorial syntheses. Here a variety of different tags are used for various synthetic steps. Release and chemical identification tags are used to fingerprint the specific chemical synthesized. This approach has the advantage that the tags do not have to be bound in an oligomeric or polymeric form. Therefore, the tags do not have to be sequenced. This approach has the disadvantage that the tags must be robust to all process steps and that the tags must be chemically analyzed upon completion of a binding assay.

Prior to the present invention, there has been developed a combinatorial bead which is labeled electronically, via an encapsulated electronic system. This bead, which is now being commercialized by Irori, Inc., was developed by K. C. Nicolaou and Xiao-Yi Xiao and is described in Chem. Int. Ed. Engl., 34, p. 2289 (1995), and also disclosed in International Application Number: PCT/US96/06145. In this application, the chip includes encapsulated memory devices associated or coated directly with derivatized polymer during combinatorial synthesis. The chip encodes information about the synthetic pathway, including the reagents used and the conditions of synthesis. The device can then report this information to a receiver via a radio frequency link. A related approach has been developed by Edmund Moran at Ontogen Corp. and described in J. Am. Chem. Soc., 117, p. 10787 (1995).

The Ontogen and Irori systems make use of RF transponder and readout technology developed by Bio Medic Data Systems and Avid Corporation, among others. These systems provide RF tagging capsules and tracking systems for animal and equipment monitoring. One system of this type is described in U.S. Pat. No. 5,252,962 (Urbas) and includes a passive transponder which has a receive antenna for input signals. A frequency generator that receives the input signal and outputs a data carrier signal having a frequency independent of the input signal frequency. A programmable memory and thermistor are provided to produce user identification (ID) data and temperature data which are combined with an output signal. Other systems of this type are described in U.S. Pat. No. 5,351,052; U.S. Pat. No. 5,214,409; U.S. Pat. No. 5,257,011; and U.S. Pat. No. 5,266,926.

The IRORI Quantum Microchemistry system uses an encapsulated RF EEPROM memory device which has dimensions of 8×1×1 mm. The encapsulation consists of TentaGel-like polymer beads carrying an acid-clevable linker to nucleate synthesis of a peptide library of compounds, and a chemically inert, surrounding porous support. Internally the bead includes a memory and temperature sensing unit encapsulated in glass. The memory device is completely passive. Power is provided to the RF systems via magnetic inductive coupling to an antenna coil wound around a ferrite core. The antenna is encapsulated with Rectifier/ regulator, frequency generator and data logic, electrically erasable logic and thermal sensing chips.

The primary size limitation in the RF chip approach is related to providing power to the chip, and placing transmission antennas directly and inexpensively on the RF chip. Off chip batteries can be used or magnetically coupled power as in the previously described embodiments are possible. To date, planar antennas have been inefficient and cannot couple enough energy into the chip to power the device. Recent advances in planar antenna fabrication technology hold the promise of the availability of integration of transmission antennas that operate at up to 40 Ghz with CMOS circuitry. Work of this type is described in the Nov. 25, 1996 issue of Electronic Engineering Times. However, even with such antennas, it is impractical for chips to be powered by RF or microwave beams because such chips cannot be made small enough to be useful.

All of the above-described devices have limitations that restrict their usefulness. One major limitation of these devices is a lack of durability associated with their size and weight. If, for example, the beads include an on-bead power source such as a battery, they will be so large and heavy that they are unlikely to long survive the jostling associated with movement through a sequence of reaction vessels. Even if the beads include an off-chip power source, the on-chip energy coupling devices such as the ferrite core and associated pickup coil again make the bead so heavy that it is unlikely to long survive processing through a sequence of reaction vessels. Attempts to replace such cores and coils with microwave power receiving antennas result in inadequate received power levels even when those antennas are made so large as to make the associated chips unwieldy.

Another approach to combinatorial tagging is to physically mark each bead with an encoding mark at each synthetic step in the combinatorial process. This approach is exemplified by the "optical spectral hole burning" system described in IRORI PCT filing number PCT/US96/06145. Optical spectral hole burning uses an intense laser beam to burn a hole in the absorption spectral profile of a suitable material. Spectral hole burning may be present only during the laser pulse, or be a long lasting phenomenon. For use in a bead marking system the absorption hole must be long lasting, and insensitive to all temperature excursions that the bead may undergo during synthesis. A spectral hole burning system for use as an optical memory is described in U.S. Pat. No. 5,136,572. The key to a long lasting realizable optical spectral hole burning system is the availability of a material with an inhomogeneously broadened absorption spectra that supports the availability of many spectral holes at the same spatial position. Materials exist that satisfy these conditions at low temperature, but not at room or elevated temperatures. A few spectral holes may be generated at room temperature. Thus synthetic information must be encoded in a geometrically defined series of independent spectral holes. This is not a robust encoding scheme, and it is not clear whether the spectral holes are stable to all synthetic conditions.

Many combinatorial synthetic protocols use between $10^2$–$10^6$ beads. It is advantaged to provide each bead with its own predetermined (or permanent) ID tag. The tagging mechanism may be electromagnetic, or physical. Examples of physical tags include bar codes and alphanumeric codes as described in IRORI PCT filing number PCT/US96/06145.

Specifically, the IRORI PCT captures the concept of using alphanumeric marks and bar codes as ID codes for tracking combinatorial beads, claiming an alphanumeric code or a bar code, as well as tagging a "matrix" with an identifying mark. Marking synthetic matrices with bar codes or alphanumeric markings requires an imaging readout of the code before each synthetic step. This is not always practical with small beads that are not completely oriented, and information extraction from an image may take a substantial time period. Other tagging schemes disclosed here are more advantaged.

In view of the foregoing, it is seen that a need exists for a mobile tracking device which is small and inexpensive to produce, which does not require the use of batteries or radio or microwave links, is easy and fast to read, and yet which is both durable and able to perform all of the functions required of it during its use in a combinatorial synthesis apparatus.

The invention of this patent is a bead tagging device that emits an electromagnetic wave whose spectrum is alternatively a distinct combination code, a distinct permutation code, and a distinct permutation code whose separate temporal components may be a combination code; and whose spectrum therefore distinctly identifies each bead. The invention of this patent is furthermore a terminal apparatus that receives that spectrum and distinctly identifies each bead. The invention of this patent is furthermore a method for bead identification that uses the bead tagging device and terminal apparatus of this invention. The precise meaning of a combination code and a permutation code with respect too this invention are described presently.

A combinatorial chemistry bead ID Tag with an electromagnetic combination, permutation, or combined permutation/combination identifying code should satisfy the following conditions: 1) the frequency of each spectral component in the tag must be distinct from all other spectral; 2) the efficiency of emission of each spectral component must be high enough to ensure reliable detection, with a high Signal/Noise ratio; 3) the tagged bead should be small, less than 2 mm in its largest physical dimension; 4) the entire ID code for each bead must be transmitted and verified in less than 50 milliseconds; 5) the tag system should allow spatial localization of ID code readout, consistent with high speed identification and sorting; 6) the stimulus signal should be able to be applied to all orientations of the bead that the bead may acquire during the ID tag reading process; 7) the tag emission spectral signature should be non-directional, or controllable to allow reliable readout or be consistent with a readout system that acquires signals from all relevant directions of emission; 8) the stimulus and ID spectral signatures must not significantly interfere with, or cause damage to, the growth of, or assay of, molecules on the combination synthetic bead; 9) the stimulus and ID spectral signatures must not be significantly absorbed by the fluid, or vessel in which the bead is disposed during readout; and 10) the tag system must be stable under all temperature, pressure and fluidic environments the bead may encounter during synthesis, readout, assay, and storage.

SUMMARY OF THE INVENTION

Accordingly, it is an object of this invention to overcome the limitations and drawbacks of the prior art by providing a combinatorial chemistry identification device and method that is not dependent upon the direct structural determination of the oligomeric compounds or upon a photochemical linkage of peptides and nucleotides.

Accordingly, it is an object of this invention to overcome the limitations and drawbacks of the prior art by providing an apparatus and method for bead tagging that is not dependent upon a bead tag apparatus that includes recording structures on the bead for recording the synthetic pathway that the attached oligomeric compound undergoes, is not dependent upon a power supplying apparatus on the bead for operating that recording apparatus, is not dependent upon recording the synthetic pathway that an attached oligomeric compound undergoes, and is not dependent upon receiving that recorded information pathway from the bead.

Accordingly, it is an object of this invention to overcome the limitations and drawbacks of the prior art by providing a distinct ID tag for each bead and a method for using that bead, that does not comprise a chemical moiety and is hence not disadvantaged by the slow and complex identification process of a chemical moiety tag, and the possible incompatibility of the chemical stability of the moiety and the synthetic process.

Accordingly, it is an object of this invention to overcome the limitations and drawbacks of the prior art by providing a distinct ID tag for each bead, and a method for using that bead, that is not dependent upon the narrow orientation range of a physical mark or of a passive color coded mark that merely reflects radiation.

An object of this invention is to provide a distinct ID tag for each bead, and a method of using that bead, that is an electromagnetic spectral code—combination, permutation, or combined permutation-combination—that distinctly tags each bead of a combinatorial library.

Another object of this invention is to provide a distinct ID tag for each bead of a combinatorial library, and a method of using that bead, that is an electromagnetic spectral code in which the wavelength band of the spectral code is in the wavelength band of light.

Yet another object of this invention is to provide a distinct ID tag for each bead of a combinatorial library, and a method of using that bead, that is an electromagnetic spectral code in which the wavelength band is in the wavelength band of light, and in which the emitted wavelength band is narrowed to provide a sufficient number of distinct spectral codes for a combinatorial library.

Still another object of this invention is to provide a distinct ID tag for each bead, and a method of using that bead, that is an electromagnetic spectral combination, permutation, and combined permutation-combination code where the efficiency of emission of each spectral component is adequately high to ensure a strong electromagnetic emission.

Yet a further object of this invention is to provide a combinatorial bead and a method of using that bead, that is small, less than 2 mm in its largest physical dimension.

A still further object of this invention is to provide a distinct ID tag for each bead, and a method of using each bead, whose ID data is transmitted in less than 50 milliseconds.

A still further object of this invention is to provide a distinct ID tag for each bead, and a method of using each bead, that allows spatial localization of ID code readout consistent with the high speed readout requirement of the combinatorial synthesis process.

A still further object of this invention is to provide a distinct spectral ID tag for each bead, and a method of using each bead, where the external stimulus signal for spectral emission can be applied in all orientations that the bead may acquire during a readout process.

A still further object of this invention is to provide a distinct spectral ID tag for each bead, and a method of using each bead, in which the spectral emission of each bead allows emissions from all relevant directions.

A still further object of this invention is to provide a distinct spectral ID tag for each bead, and a method of using each bead, in which emission and external stimulus signal for that emission do not interfere with or cause damage to the growth or assay of the attached oligomeric compound.

A still further object of this invention is to provide a distinct spectral ID tag for each bead, and a method of using each bead, whose spectral emission and external stimulus signal is not significantly absorbed by the fluids and chemicals of the combinatorial process.

A still further object of this invention is to provide a distinct ID tag for each bead, and a method of using each bead, that is stable under all temperature, pressure, and fluidic environments that the bead may encounter during combinatorial synthesis, readout, assay, and storage.

These and other objects of the present invention are attained by a bead that includes an electromagnetic spectral emitter that radiates a predetermined electromagnetic spectrum, comprising at least one wavelength band, and in which a plurality of beads of a number large enough to comprise a combinatorial bead library each radiate a distinct combination, permutation, or combined permutation-combination code of wavelength bands, so that each electromagnetic spectrum distinctly identifies each bead. To emit the large number of possible frequencies required by a combinatorial bead library, the electromagnetic spectral emitter of this invention includes a large number of spectrally narrowed distinct wavelength band embodiments.

The invention furthermore includes a terminal apparatus that receives the electromagnetic spectrum of each bead, identifies each wavelength band of the emitted code, records that code, identifies each bead distinctly, and records each identification as each bead undergoes the combinatorial synthesis process.

The invention further includes a method of tracking combinatorial beads in which the beads have an electromagnetic spectral emitter of this invention and a terminal apparatus of this invention.

More particularly, the signal emitted by the bead includes distinct electromagnetic frequency components selected from a set of allowed frequency components that are used to encode a set of bead Identification codes. In one embodiment of the invention, the spectral components are emitted simultaneously and is designated a combination code. In another embodiment of the invention, the spectral components are emitted sequentially and is designated a permutation code. In a third embodiment of the invention, multi spectral components are emitted by the bead both simultaneously and sequentially, and embody a hybrid permutation-combination code.

Combination spectral code tag embodiments of the invention take advantage of a natural emission of frequency shifted radiation by chemical and physical systems after absorption of input electromagnetic radiation, as a mechanism for generating encoded combination spectral tags. Both stimulus radiation and coding radiation preferably is in the optical and near infrared regions of the electromagnetic spectrum. Examples of natural frequency shift emissions include electronic energy level radiative transitions that result in fluorescence emission from atoms, ions, and molecules; Raman optical emission from vibronic and rotational states of molecules; and excitonic emission from electron and hole recombination in semiconductors. Each of these emissions include characteristics that prevent their direct implementation as spectral emitters in a combination code. These processes either emit with too low an efficiency, or emit with too large a bandwidth to allow the separation of the 20–30 individual frequency components required for a combination code. Man-made constructs are therefore combined with the naturally emitting frequency shifting emission mechanisms to enable combination spectral coding. These provide for spectral tuning, spectral narrowing, and emission efficiency enhancement. The man made constructs of the invention include micro optical cavities, grating, Bragg reflector and scattering particle feedback systems, and microspheres. Additional man made constructs of the invention that enable combination spectral coding include photoelectric cells which provide power to electroluminescent micro light emitting diode and laser structures.

Permutation frequency encoded tag systems have all the capabilities of combination systems, and additionally provide time sequence encoding of the frequencies of emission. Time sequencing of output frequencies requires the intervention of an electrical circuit between the input radiation field, and the electromagnetic spectral emitter. It is required to keep the circuitry small, and simple. Therefore, the permutation encoded bead embodiment of the invention includes a simple sequencing circuit to provide the correct sequence of emission frequency components. The toggling signals required to sequentially strobe out encoded ID information are preferably provided by the terminal apparatus.

The ID tagging device is a constituent of the bead. The other parts of a combinatorial chemistry bead includes a molecular anchoring site for attachment of an oligomeric compound (molecule) undergoing synthesis on a bead. The growth matrix attaches to a molecular anchoring site, which attaches to the oligomeric compound itself or alternatively attaches to a linker group which attaches to the oligomeric compound. In distinct embodiments of the invention, the growth matrix is attached to the ID tag, or encapsulates the ID tag. The ID tag may be permanently or detachably connected to a single growth matrix, allowing replacement with a new growth matrix for use in different synthetic protocols. The growth matrix is disposed of after a single use, or washable for multiple syntheses.

The invention furthermore comprises an associated terminal apparatus. The terminal apparatus emits an electromagnetic radiation signal that provides power to the bead tagging device, and causes the bead tagging device to emit an electromagnetic spectrum which provides a unique Identification signature for that bead. The terminal apparatus additionally functions to receive, decode, and store bead ID tag spectral code information, and the data related to the reaction steps to which a bead has been exposed. In the preferred embodiment of the invention, the electromagnetic radiation of the electromagnetic spectrum emitter, and of the terminal apparatus, are both in the wavelength band of light.

The combination of the above-mentioned optically coupled terminal power supply structures and optically coupled communication devices affords the bead of the invention significant advantages over the most nearly similar previously known beads. In the case of the optically coupled power supply structures these advantages include the higher power densities that are possible as a result of the fact that visible (or near visible) radiation is more readily focused over a small area than either radio or microwave radiation. In the case of the optically coupled communication devices these advantages include the smaller transmitting and receiving areas and higher data transmission electromagnetic radiation bandwidths that are made possible by the use of visible or near visible wavelengths. These advantages, in turn, make possible the use of many more beads per experiment.

In summary, the apparatus of the invention has several significant improvements over previously known apparatuses for tracking combinatorial synthesis. Firstly, electromagnetic radiation frequency encoded ID tagging is used. Optical radiation frequency encoding and communication is preferred. Therefore, the tagged bead is small (less than 2 mm in diameter) and is spatially localizable on the scale of several tens of microns. This allows for easy and rapid decoding of bead ID number, and sorting of beads via devices such as fluorescence activated cell sorters, and rapid fluid flow streams. Bead decoding and cataloging may occur in less than 50 milliseconds per bead per synthetic step. Secondly, combination coding schemes takes advantage of natural frequency shifting mechanisms, or simple arrays of man made structures, in a very small format. This ID encoding approach is used to catalogue greater than $10^8$ beads. Thirdly, permutation coding schemes use simple optically powered circuits to emit an electromagnetic radiation frequency code. These codes are used to code for greater than $10^9$ beads. Fourthly, encapsulation provides for protection ID tag components from all synthetic conditions. Fifthly, together with the on-bead ID tag, encapsulation and chemical growth matrix endow the bead with the ability to take part in and track the results of a series of synthetic reactions, in conjunction with and under the overall control of one or more external terminal devices, to identify and catalogue very complex sequences of synthetic and analytic steps, and thereby facilitate the production of wide variety of new or improved compounds. Accordingly, it will be seen that, in its broadest aspect, the bead portion of the apparatus of the invention comprises an electromagnetic radiation powered, fully submersible, reusable platform of near microscopic size for use in tracking combinatorial synthesis processes.

DESCRIPTION OF THE DRAWINGS

Other objects and advantages of the invention will be apparent from the following description and drawings, in which:

FIG. 9 is a side view schematic of an exemplary LED array wherein each LED emitter is surrounded by a resonant cavity in order to narrow the emitted wavelength, and where each spacer is distinct so that the emitted bandwidth of each LED emitter is distinct;

FIG. 10 is a side view schematic of an exemplary LED array wherein a high refractive index layer is disposed on top of an LED emitter, with a Fabry-Perot Etalon structure filter disposed on top of the low refractive index layer, to narrow the wavelength band of each LED emission, so that it can function as an ID tag spectral emitter;

FIG. 11 is a side view schematic of an exemplary LED array wherein a low refractive index layer high is disposed on top of an LED emitter, with a multilayer filter disposed on top of the high refractive index layer, to narrow the wavelength band of each LED emission, so that it can function as an ID tag spectral emitter;

DESCRIPTION OF THE PREFERRED EMBODIMENTS

Figure 1A:
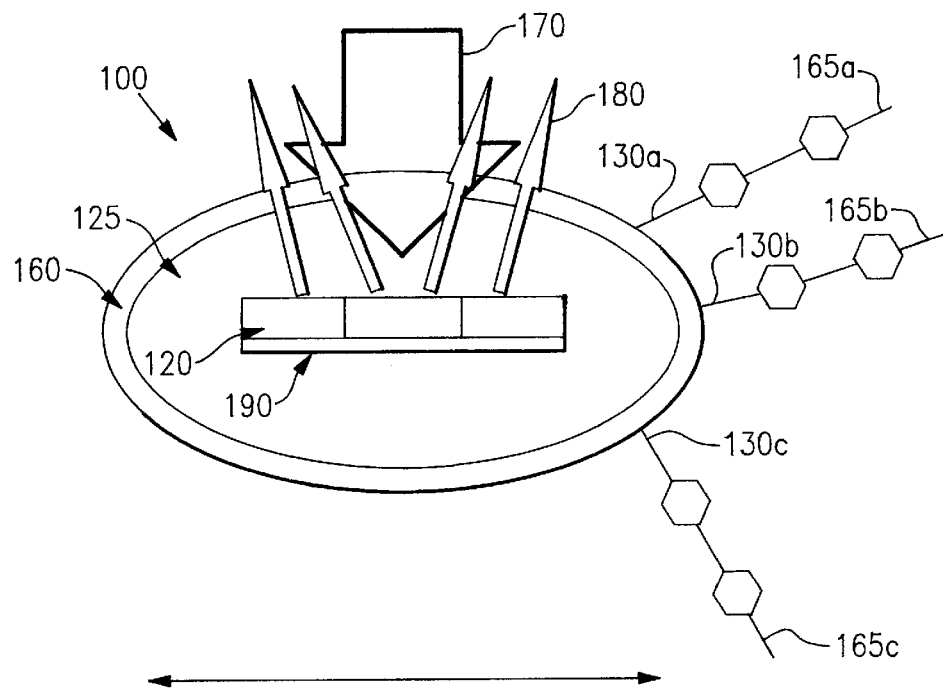
FIG. 1a is a greatly enlarged simplified cross-sectional view of an encapsulated tracking bead and the attachment of the encapsulate to a growth matrix.

The present invention comprises a mobile transport bead (bead) that attaches to an oligomeric compound during a combinatorial chemistry reaction sequence. That bead includes an electromagnetic spectrum emitter that radiates an electromagnetic spectrum comprising at least one radiation wavelength band that uniquely identifies each bead and the at least one attached oligomeric compound. The radiation wavelength band(s) comprise alternatively a simultaneous combination code, a sequential permutation code, and a combination thereof.

The bead is separated, sorted and rerouted as a conveniently handled unit. A bead of this type is ordinarily used in large numbers that are processed simultaneously in the same reaction vessel, or in parallel into different reaction vessels. During a series of synthetic steps, these beads are combined, separated and recombined in new combinations as they pass through a series of reaction vessels to produce a number of different end products simultaneously.

The ID tag embodiments constructed in accordance with the invention can easily accommodate the $10^6$ or greater independent identification (ID) tag spectral codes that a combinatorial synthesis requires.

Definitions

As used herein, a bead is the platform upon which the combinatorial chemical reactions of this invention are performed. A bead may be any convenient shape and include pins, wells, raised regions, etched trenches, and other surface shapes. The term "beads" include pellets, disks, fibers, gels, particles pads, slides, films, matrices, etc. A bead state may be solid, porous, rigid, semi-rigid, deformable, hard, etc. Bead material may be any convenient composition that maintains the mechanical integrity of a bead, is compatible with the chemical reagents and reactions to which a bead is exposed, and which is relatively transparent or at least translucent to electromagnetic radiation within the bands of wavelengths over which it will be used. A bead surface composition may include cellulose, glass, pore-glass, resin, silica, polystyrene, the material of the Identification tagging apparatus, and composite coated with a hydrophobic polymer.

As used herein, combination spectral codes are an order independent, simultaneous emission of a selection of a set of radiation frequencies, from an ensemble of possible emission frequencies, for encoding the ID number of a bead.

As used herein, permutation spectral codes include the additional variable of the time sequential order of emission of the frequency components into the determination of the different ID codes.

For combination spectral codes the number of possible tags is computed by a standard combination calculation. Each frequency component is independently recorded. For example, if 6 out of 30 possible emission frequencies are used to tag each bead, then 593,775 unique identification codes are possible. If 6 out of 40 possible frequencies are emitted, then 3,838,380 unique tags are possible, while using 10 out of 40 possible frequencies then 847,660,528 coded tags can be generated. Therefore, combinatorial tagged libraries of beads of $10^9$ are readily possible.

An alternative representational method of using a combination spectral code is to have each frequency component (or wavelength band) represent a given bit in a n bit binary number. When the frequency component represents a distinct visible light color, the absence of the color in the decoded ID tag number represents a 0 and the presence of a color represents a 1. A 40 bit number can encode $10^{12}$ tags. Parity bits can be included to help in error correction. Alternative error detection and correction approaches include the use of 2 colors to represent the 1 and 0 levels. In this case 40 colors represent 20 bits, which may encode 1,048,576 tags.

For a permutation code, standard permutation calculations are used to calculate the number of possible tags, where a single frequency component can not be repeated. If repetition of frequency components is allowed, the number of possible tags is given by:

$$(\text{\# of possible frequencies})^{\text{\# of positions in code}}$$

If 6 out of 30 possible frequency components are used in a permutation code, then 427,518,000 possible unique ID signatures are possible, without allowing for a repetition of a frequency component. If repetition of components is allowed, then 729,000,000 tags are possible. If 6 out of 40 possible frequency components are used in the code, then 2,763,633,600 ID tags are possible, without allowing a repetition of a frequency component. Clearly, a permutation code can encode a larger number of unique signatures than a combination code. Permutation codes are advantaged because fewer frequency components are required to encode a given number of beads. However, time sequencing of spectral emissions usually requires the interposition of an electronic circuit. This circuit provides clocking, sequencing, and turning on and off of the sequential electromagnetic frequency component emissions. Therefore, the electrical control adds to the complexity of a tagging system embodiment.

A permutation code may (in the limit of fewest frequency components used in the code) be expressed as a long sequence of the presence or absence of a single frequency component, or the alternating presence of 2 frequencies. This is a traditional binary code. In a bead embodiment that uses this particular coding system, allowance for repetition of the frequency components must be made. A binary permutation code of 32 positions can code for 4,284,967,296 unique identification tags. Therefore permutation coded libraries can number more than $10^9$ beads. Using permutation codes, combinatorial bead libraries are limited in size by the cost of bead production.

As used herein, a laser medium consists of ions, molecules, atoms, or energy bands, in a semiconductor that are able to support the process of amplified stimulated emission. Photons are emitted by excited states in the preceding structures (ions, molecules, atoms, or energy bands), and are added to an already populated radiation mode of an electromagnetic field. These constructs may be suspended in a host material, such as a crystal, plastic, glass, or buffer gas in order to facilitate the process of amplified stimulated emission. Adding photons to specific radiation field modes narrows the emission spectrum of a lasing medium and facilitates the construction of the ID tags described herein.

Bead Embodiments

The bead itself serves a function of providing a support platform for at least one oligomeric compound and providing a spectral identification tag to the attached oligomeric compound. The bead includes a spectral ID tag comprising an electromagnetic spectrum emitter, and any required power absorption device and required permutation code sequencing device that a specific embodiment may require. (As explained presently, a permutation code requires a sequencing device and also a power absorption device to supply power to the sequencing device, and some electromagnetic spectrum emitters require a power absorption device to supply power to the emitters). The bead additionally includes a molecular anchoring site attached to a molecular growth matrix that adheres to an oligomeric compound. The ID tag may or may not be encapsulated depending upon its embodiment.

Figure 1B:
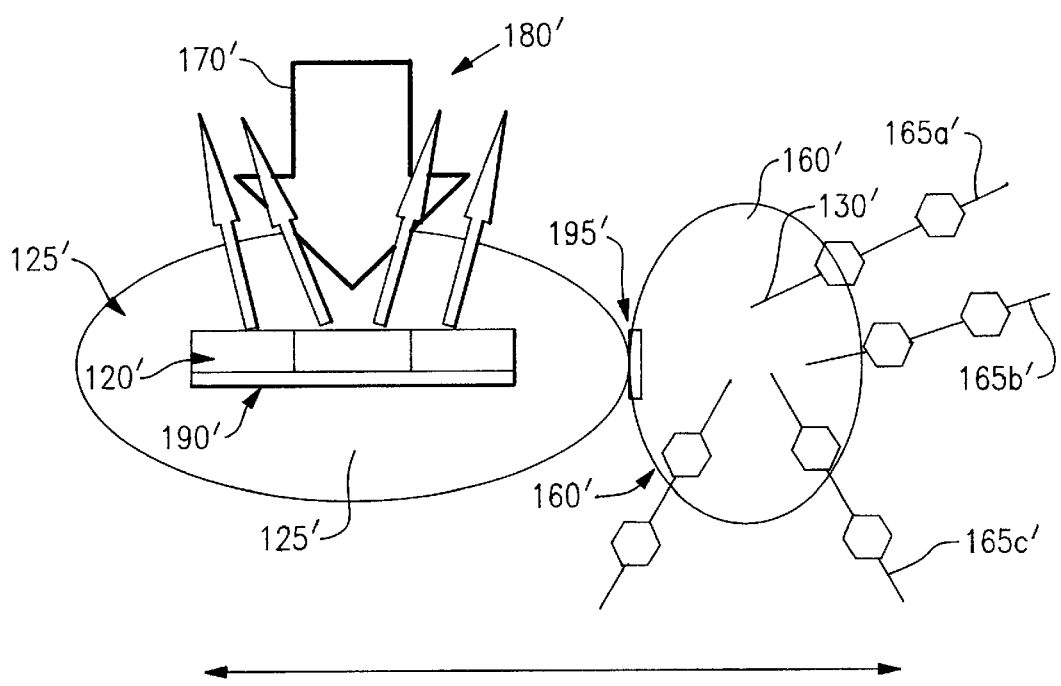
FIG. 1b is a greatly enlarged simplified cross-sectional view of an unencapsulated tracking bead and the attachment of an ID tag to a growth matrix.

FIG. 1A and FIG. 1B distinguish between a growth matrix that fully an ID tag and a growth matrix that attaches to a side of an ID tag, with similarly functioning elements in FIG. 1B being numbered with a prime ('). Referring to FIG. 1A, the bead 100 includes an ID tag 120 that is surrounded by a protective encapsulant 125 and molecular anchoring sites 130a–130c that are attached at a plurality of sites on the growth matrix 160. Referring to FIG. 1B, the growth matrix 160' is not surrounding the ID tag 120' but is attached to the growth matrix at an at least one site 195' on the ID tag 120' itself. In either embodiment, the molecular growth matrix 160 and 160' is removable from tag 120 and 120' respectively, and replaced or regenerated to allow reuse of the ID tag in a new combinatorial protocol. The ID tag is protected from the synthetic chemical environment by encapsulant 125. The ID tag is fabricated on substrate 190.

The molecular growth matrix is composed of cross linked polymeric structures, nonporous or porous glass, or other such materials that non-interferingly adhere to the oligomeric compounds. The molecular growth matrix has a molecular anchoring site 130 for attachment of linker groups to which growing oligomeric compounds 165a–165c may be attached or alternatively the oligomeric compounds 165a–165c may be directly attached to the growth matrix itself. The growth matrix may be attached to the ID Tag by chemical cross-linking, mechanical complementary surfaces, or other such means known to those skilled in the art. Powering light 170 provides energy to enable the emission of the electromagnetic spectral ID code 180.

Glass or plastic encapsulant 125 is formed over, or at least secured over, ID tag 120 after the fabrication of the ID tag is completed. If encapsulant 125 is formed over ID Tag 120, it is preferably formed by the sputtering or vapor deposition of silica or A polymeric material in a manner known to those skilled in the art. If encapsulant 125 is to be merely secured over the ID tag 120, it may be formed from one or more separate pieces of glass, or plastic which define ID tag receiving cavities, and which are then joined together and sealed after the ID tag has been inserted into and fixed in place within those cavities. It will be understood that the manner in which encapsulant 125 is made to encapsulate ID tag 120 is unimportant as long as encapsulant body 125 is able to protect ID tag 120 from exposure to the media and reactants with which it will be used, and as long as body encapsulant 125 is adapted to transmit (with or without scattering) photons having wavelengths within the wavelength bands which it will be used.

It will be understood that, for most applications, it is unimportant whether there are one, two or even more layers of encapsulating material separating ID tag 120 from the surface 195 of bead 100. Accordingly, the term "encapsulant" will be use herein generically to refer to all of those layers, without regard to their number, except where otherwise indicated.

Unlike prior art tracking beads, bead 100 is not merely an inactive mobile transport platform for the molecules anchored on the surface thereof. In particular, the tracking bead of the invention is equipped and able to operate not only as a mobile transport platform, but also is equipped and able to operate as an optically powered electromagnetic spectrum emitter for radiation of a distinct electromagnetic code. In accordance with the invention, this ability to so operate is made possible by taking advantage of the transparency of encapsulant 125 to photonic and other electromagnetic radiation, and by endowing ID tag 120 with the ability to operate entirely on operating power that is received photonically through that body.

Permutation encoded ID tags have a capability of time sequence encoding of the frequencies of emission. The preferred embodiment of a permutation code emitting bead includes an electrical circuit for storage of the temporal sequence and components of a permutation code, a photodiode for receiving a transmission from the terminal apparatus to trigger and to toggle the radiation of the permutation code by an electromagnetic spectrum emitter, and a photoelectric cell to receive energy to power the electric circuit and electromagnetic spectrum emitter.

Figure 2:
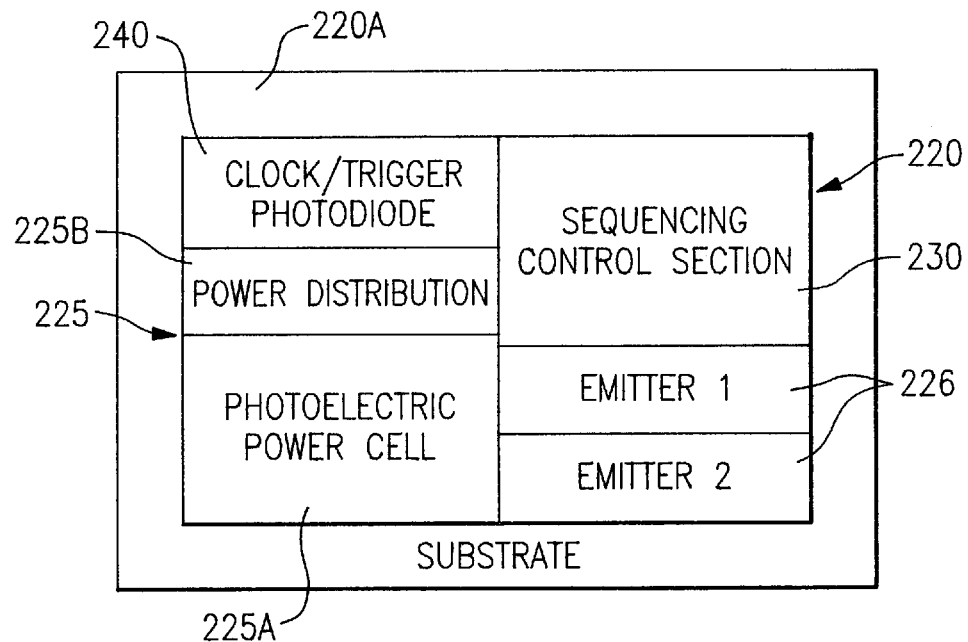
FIG. 2 is an embodiment of a bead ID tag electrical circuit apparatus and power absorption apparatus, without encapsulating material.

Referring to FIG. 2, a preferred embodiment of a bead with an electrical circuit apparatus and a power absorption apparatus are presented diagrammatically, wherein all encapsulating material has been omitted for the sake of clarity. Also omitted from FIG. 2 for the sake of clarity are individual circuit elements and electrical conductors which connect the same both within and between functional sections thereof.

As shown in FIG. 2, ID tag 220 is in the form of a chip and includes a substrate 220A, which may be composed of any material which is compatible with the fabrication of solid state integrated circuit elements by means of known deposition techniques and materials. Such deposition techniques include one or more of epitaxial deposition, chemical vapor deposition, electroplating, thermal deposition in an amorphous phase and spin coating, among others. Combinations of such deposition techniques may be used provided they are compatible with one another. For present purposes compatible techniques are those which allow the adhesion of the over-lying and underlying layers, the non-dissolving of one layer in another, the stress matching of layers, and the thermal compatibility with other process steps and dopant choices.

The most commonly used material which may be used for this purpose is presently silicon. However alloys of GaAs, and glass based structures are also used. Accordingly, the processing techniques used to produce ID tag 220 will be understood to refer to general semiconductor processing techniques, except where otherwise indicated.

Deposited on substrate 220A are a plurality of spatially separated functional units or sections which have different respective functions and which may include individual components such as transistors, resistors, capacitors, photodiodes, photoelectric cells, and electromagnetic radiation emitters, preferably light emitters. Included among these functional sections are a power assembly section 225 which includes a photoelectric power cell 225A and a power conversion/distribution unit 225B. The photoelectric cell receives electrical energy through the encapsulant from an external source and converts that energy directly into electricity. The electricity is then converted to voltages and currents of usable magnitudes and distributed to the remaining sections of ID tag 220 by the power conversion/distribution unit 225B. In order to allow ID Tag 220 to continue to operate when no light is incident on photoelectric cell 225A, power assembly section 225 also preferably includes an energy storage capacitor (not shown) which charges when photoelectric cell 225A is being irradiated by the external source, and which discharges, as required, to the remaining componentry of ID tag 220.

Photoelectric cell 225A may include an array of p-n silicon junctions with a single bandgap energy $E_g$. The bandgap for silicon at 300 degrees K is 1.12 electron volts (eV), while that of GaAs is 1.45 ev. An absorbed photon with energy greater than the energy $E_g$ contributes only $E_g$ to the cell output, the excess energy being dissipated as heat. In solar cell applications this is of critical importance in determining cell efficiency. In this application the bead electronics may be powered with a laser diode with an emission spectrum composed of a single line with photon energies from 1.26 to 1.55 eV (0.98 μm to 0.8μ), or within 10–30% of the bandgap energy. Therefore, most of the photon energy will be collected by the solar cell, and light conversion efficiency can be substantially in excess of 50%.

As described by Sze in *Physics of Semiconductor Devices*, 2nd Edition, Wiley-Interscience New York 1981 p. 790–838, a photoelectric cell can be represented by the ideal current-voltage (I-V) curve of a diode junction. This is given by:

$$I = I_s(e_q v/kT - 1) - I_L,$$

where $I_s$ is the saturation current, $e_q$ is the charge on an electron, v is the voltage across the diode junction, k is Boltzmann's constant and $I_L$ is the source current that results from excess carriers generated by light radiation. With sufficient photo-generated carriers the diode voltage is about 0.5–0.6 volts for Si and above 1 volt for GaAs. Therefore to drive memory, or an electroluminescent device at 5–12 volts requires placing 10–25 diode junctions of Si and 5–12 junctions of GaAs in series, as is normally done in solar power systems. In some applications, diode junctions may be formed on both the upper and lower surface of substrate 20A.

The $I_s$ for a junction is equal to the current density divided by the device area ($J_s/A$). $J_s$ is a function of various materials characteristics of the cell, as described in Sze. The total device area A used for this application is at most 1 mm² which leads to a $I_s$=2.5 picoamps.

As will be explained more fully later, tracking beads of this invention may be caused to emit their electromagnetic ID code in a microtiter plate, vial or other vessel, or in a flow cell system. The preferred external illumination source is a laser and is assumed to be a laser diode array that produces 1–5 watts of light such as is commercially available from SDL, Inc. (San Jose, Calif.). The laser diode is focussed on the bead to a power density of 1–5 watts/cm². If the conversion efficiency of photon energy into electrical energy is 50%, and if the photocell is operating at 10 volts, a 1 mm² area photocell will generate 1–5 milliamps of current.

Power conversion/distribution unit 225B is of a conventional type and operates by generating, from the voltage across an energy storage capacitor, a plurality of stepped down voltages having magnitudes suitable for operating the circuit elements to be powered thereby. Examples of such stepped down voltages are voltages in the range of 3–5 volts for operating control logic, and 5–10 volts for operating light emitting diodes 226. Because of the overlap between the range of voltages, a single voltage source may be used for multiple functions. Examples of circuits suitable for use as step down circuits include series and parallel voltage regulator circuits and zener diode regulator circuits, among others. Because such circuits are well known to those skilled in the art, they will not be described in detail herein.

Also included among the functional units deposited on substrate 220A is sequencing control section 230, which serves to control and coordinate the operation of ID Tag 220. Its functions typically include toggling (or clocking functions), and communication functions including data decoding.

Sequencing control section 230 is preferably fabricated with standard complementary metal oxide semiconductor (CMOS) components because of their low current requirements and advantageous scaling properties. Preferable the toggling circuitry is driven by a signal derived from the terminal apparatus and received by photoreceiver section 240. External toggling (preferably by the terminal apparatus) reduces the complexity of on-tag circuitry. Less preferably the toggling circuitry may be implemented by means of a simple digital oscillator, such as a free-running multivibrator, that does not include a frequency setting crystal. The use of such an oscillator is desirable because it simplifies the fabrication of the chip, and because the precise pulse frequencies associated with crystal oscillators are unimportant for purposes of the present invention.

The photodiode or photodiodes of photoreceiver section 240 can comprise silicon, GaAs, organic semiconductor photodiodes, and photodiodes structure of the type described in *Physics of Semiconductor Devices*, 2nd Edition, 743–787, Wiley-Interscience New York (1981). Other structures that can be used include p-I-n and avalanche diodes. The communication wavelength may be chosen to be in the red or infrared band. Megahertz speeds will be readily achievable, although in most applications not required.

In the embodiment of FIG. 2, light emitting diodes 226 transmit to an external terminal apparatus optical spectrally encoded ID tag data produced by control and sequencing section 230. If only one transmitter diode is used, this data will necessarily be transmitted serially. If two or more transmitter diodes are used, this data may also be transmitted in parallel in a multi-bit or multi-wavelength code, that is a mixed combination—permutation code. Encoding information in more than one wavelength reduces the number of pulses that must be transmitted to the terminal apparatus.

In fabricating the above-mentioned transmitting photodiodes, it is important to use a light emitting structure with the chosen substrate that may be electrically driven. Particular suitable light emitting structures include polymer light emitting diodes as described in U.S. Pat. No. 5,558,904 (Hsieh et al.) and metal chelate electroluminescent devices such as those described in U.S. Pat. No. 4,539,507 (Van Slyke et al.). Porous silicon light emitting sources may also be used. Metal chelate structures are particularly attractive for this application. They require drive voltages under 10 volts, are 5% efficient (Tang and Van Slyke, *Applied Phys. Lett* 51, 914 (1987)) and can be fabricated in separate structures that each emit a distinct wavelength band from red to blue. (See for example, U.S. Pat. No. 5,141,671 (Bryan et al.) and U.S. Pat. No. 5,409,783 (Tang et al.), and the section described RCLED structures of this patent. Additional structures include various forms of GaAs LEDs, polymer LEDs, and semiconductor lasers as described in this patent.

Less preferably the permutation ID tag may be fabricated on a plurality of separate integrated circuit substrates mounted on a passive support substrate to form a unitary physical structure. This unitary structure includes wires bonded to bonding pads that allow inter-substrate current flow substrates. In a multi-substrate embodiment, each circuit remains unchanged from the single substrate embodiment of FIG. 2.

In the multiple substrate embodiment, the division of the circuitry among component substrates serves to separate the power conversion/distribution unit 225B from the communication. Division along these lines is advantageous because this division concentrates the relatively large photoelectric and power storage sections of the tracking circuitry on a substrate on which these sections may be located one above the other, thereby making a most efficient use of a limited space on the microchip. It will be understood, however, that this division is exemplary only, and that the present invention is not limited to any particular number of component substrates or to any particular division of the tracking circuitry among them.

The advantages associated with the use of multiple substrates include the possibilities they create for including in the bead of the invention, circuits of types that can only be fabricated by processes that are not compatible with one another, and for including circuits that are better optimized for their respective function and/or are available as off the shelf items. The disadvantages associated with the use of multiple substrates include an increase in the size of the beads that incorporate microchips that use the same and the increased cost of assembling the microchips.

Combination Spectral Emitter Embodiments

Combination spectral code tag embodiments of this invention take advantage of a natural emission of frequency shifted radiation by chemical and physical systems after absorption of input electromagnetic radiation, as the mechanism for the emission of encoded combination spectral tags. The electromagnetic spectrum emitter of the invention include these chemical and physical systems.

Examples of natural frequency shift emissions include electronic energy level radiative transitions that result in fluorescence emission from atoms, ions, and molecules; such species confined in nanoparticles; Raman and resonance Raman optical emission from vibronic or rotational states of molecules; excitonic emission from electron and hole recombination in semiconductors or quantum confined electronic states in nanocrystals; and harmonic emission from microwave antennas. Each of these emissions include characteristics that detract from their direct implementation as spectral emitters in a combination code. In fluorescence emission, and excitonic emission, the natural frequency shifted radiation wavelength band is usually much broader than 50 NM. A combination code requires 20–30 individual components. Thus the broad band fluorescence and excitonic spectral emission precludes their direct implementation as spectral frequency emitters in a combination frequency coding. Raman optical emission has an efficiency on the order of $10^{-8}$, and thus generate a low intensity emission across a large number of radiation wavelength bands. As already identified, an ID tagging system requires a high signal to noise ratio. Thus, this combination of a weak signal strength and a large number of wavelength bands preclude the direct implementation of a Raman emitter in a combination frequency coding. Furthermore, nanoparticles emissions are disadvantaged by a weak signal, and microwave antenna harmonic emissions are disadvantaged by non optical radiation.

Man-made constructs are thus necessary to combine with the naturally emitting frequency shifting emissions to enable combination spectral coding. Presented herein are fluorescence, excitonic, and Raman system embodiments that are both properly narrow and strong. These system embodiments provide narrowing, and tuning of fluorescent spectra and enhancement of the efficiency of emission of specific spectral bands and Raman emissions. These man-made constructs include stimulated light emission from photon pumped micro-laser systems, light emitting diode pumped thin film polymer lasers, nano-particle organic semiconductors, scatter medium lasers (SMLs), stimulated Raman emission from microspherical cavities, and arrays of microcavity narrowband photoluminescent emitting structures.

Electronic circuits may also be combined with naturally emitting frequency shifting by interposing between the input and output signals a means for enabling combination spectrum encoding. Examples of electromagnetic spectrum emitters that include such electronic circuits include, small arrays of photoelectric cell powered electroluminescent light emitting diodes (LED), resonant cavity LEDs (RCLED), vertical cavity surface emitting lasers (VCSEL), and radio frequency (RF)/microwave antenna combinations.

We describe presently six embodiments of combination frequency encoded tag systems that are particularly well suited to combinatorial chemistry applications. The first is based upon the concept of scatter medium lasers (SML). The second embodiment is based upon an array of optically powered, spectrally narrowed light emitting diodes. The third is based upon spectrally narrowed optically stimulated luminescent emission in optic resonant microcavities of resonant dimension less than several microns. The fourth is based upon spherical microcavities that emit optically stimulated Raman radiation. The fifth is based upon very small vertical cavity surface emitting semiconductor lasers (VCSEL). The sixth is based upon planar waveguide plastic or polymer arrays, whose emission frequencies are defined by a fine period grating and are called distributed frequency lasers (DFL).

Scatter Medium Laser Spectrally Coded Combination Tagging System

Scatter medium lasers (SMLs) were developed by Nabil M. Lawandy and described in Photons Spectra, July 1994, p. 114–124, as well as U.S. Pat. Nos. 5,448,582 and 5,438,878. SML emit "laser-like" radiation from a mixture of gain medium dispersant and nano-particles in the 30–300 NM size range, that scatter light, and are dispersed in a host. These particles conventionally comprise Titanium Oxide. The medium is pumped with a focused several nanosecond laser pulse, conventionally a Q-switched laser pulse. There is no defined cavity. Reentrant optical paths are provided by scattering of light by the ensemble of randomly distributed nano-particles in the medium. Because scattering helps define the reentrant light paths rather than the spacing of the laser cavity mirrors as in a laser, the thickness of the medium is substantially less than the thickness of a laser with comparable gain characteristics. SML layer thickness is typically 250 $\mu$m, though in the preferred embodiment described presently, that thickness is 80 $\mu$m. SML emitting region are typically as small as 100 $\mu$m in diameter, and in the preferred embodiment described presently, that diameter is in the range 100–150 $\mu$m.

The radiation of SMLs is "laser-like" in the sense that the emitted radiation is spectrally narrowed relative to the fluorescent bandwidth of the emitting species. SMLs are not lasers in the sense that their light is emitted in all directions where in lasers that light is emitted directionally. They are properly characterized as Super-radiant light sources. The efficiency of conversion of pump radiation into narrow band emission is as high as 25%. Organic dyes are used to emit radiation in SMLs. The fluorescent bandwidth of these dyes may be wider than 100 NM, though the SML emitted radiation bandwidth is narrowed to as low as 3–5 NM. The emission peak of an SML is adjusted by changing the pH of their host medium or alternatively the dye species. SML wavelengths are tunable from 400 NM to greater than 1200 NM in 5 NM steps. Therefore, over the range of 400–1200 NM, 160 individual frequency component selections are available as a set of separately distinguishable encoding radiation frequencies in a combination and permutation spectral code. It is preferable to choose coding frequencies in the red or near infrared (650–950 NM) spectrum to minimize a possibility of radiation absorption by the oligomeric compounds. Red and near infrared emission is preferentially stimulated by green and/or red laser (530–650 NM) light, such as the emission of frequency doubled Neodymium ($Nd^{3+}$) doped Yttrium Aluminum Garnet (YAG) whose fundamental lasing wavelengths can be caused to run at 1.06 µm and at 1.313 µm.

SMLs are known to be stable at 100 degrees Centigrade. They can be encapsulated in glass or plastic, and a polystyrene matrix linked to the outside. The amorphous nature of the SML allows the lasing medium to be painted or cast on its substrate, or fabricated as a filament. The filament itself can be sectored laterally or across the lateral axis of the filament, and each sector can emit a distinct wavelength band. Overall, SML tagged beads form a cost effective solution to the combinatorial bead tracking problem.

With an SML embodiment electromagnetic spectrum emitter, each tagged bead is interrogated by a light pulse, preferably from a terminal apparatus nanosecond pulse Q-switch laser prior to entry into a chemical reaction vessel. Electromagnetic spectral encoded bead light emission is collected via lens, mirrors, or an integrating sphere, and the spectral components are separated by a standard grating spectrometer. The individual bead signature code is determined, the bead is individually identified, and the chemical reaction vessel for each individual bead is added to the bead data file stored in a terminal apparatus computer. About 30–60 beads may be catalogued per second per channel, although higher throughput configurations may be implemented. A single channel may catalogue and sort a $10^5$ bead library in 30–60 minutes. Ten parallel channels can reduce the sort time to under 10 minutes. More channels may be fabricated for larger combinatorial bead libraries of beads.

SMLs are fabricatable in many embodiments. The Spectra Science Corporation (Rhode Island) provides commercially available SMLs embodied in the form of a single lasing color monofilament, a sectored multicolored monofilament, and an ink.

Figure 3:
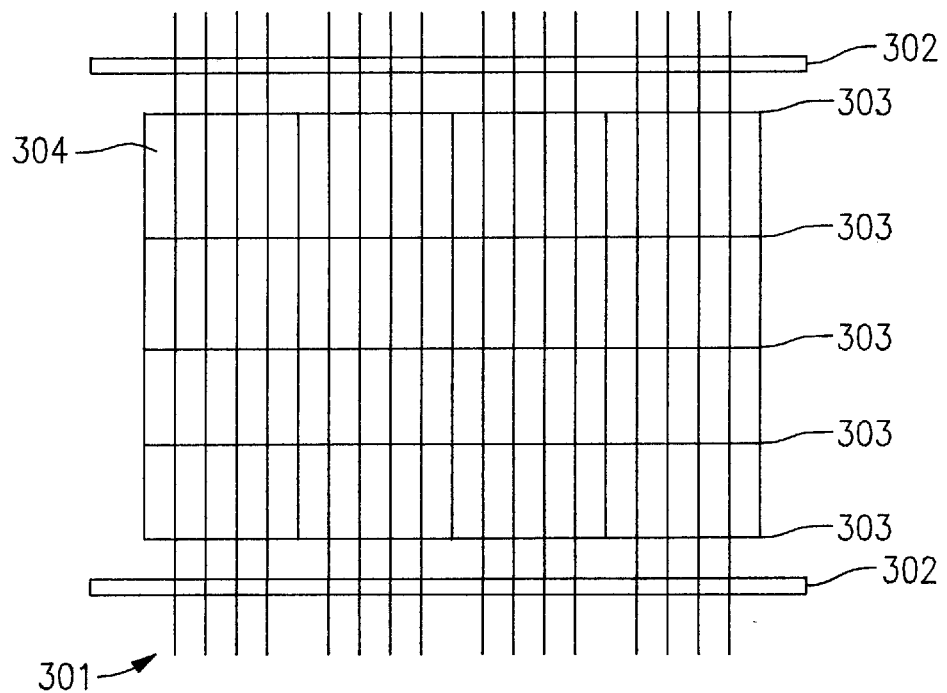
FIG. 3 is a top view of an exemplary ID tag structure formed from a scatter medium laser (SML) monofilament of four distinct color emitters.

Referring to FIG. 3, a four color binary combination code is shown although the same fabrication approach is usable for at least 20 color codes. SML monofilaments 301, each comprising one of a distinct gain medium pH or dye species, to thus emit a distinct spectral wavelength band, are stretched over two parallel attachment frames 302, thus lying in contact with an array of transparent (such as glass) rectangular tag supports 303 disposed between the attachment frames 302. Each rectangular tag support is preferably 1×1 mm². About the periphery of each rectangular tag support is a tag support frame 304. About the periphery of each rectangular tag support 303, and within each rectangular tag support's associated tag support frame 304, is laid down a bonding material (not shown) patterned by standard lithographic means. The SML monofilaments are caused to adhere to the bonding material by alternatively thermal or photonic means. Individual ID tag spectral codes are generated by laser transecting and removing individual color filaments, from individual tag frames, to thus produce a collection of all possible combination codes of the four distinctly emitting SML monofilaments.

Figure 4:
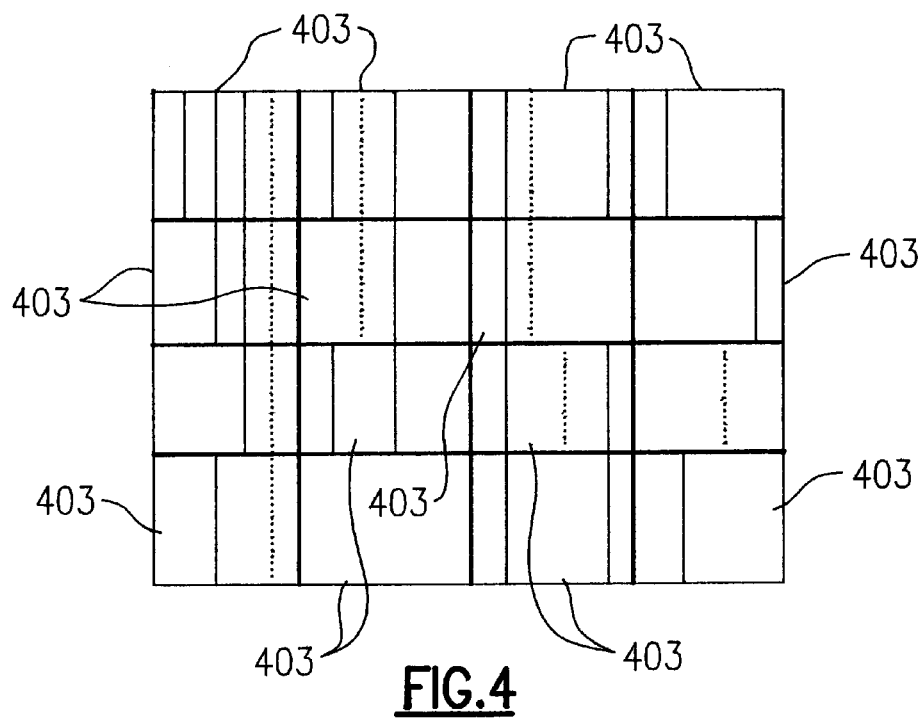
FIG. 4 is a top view of an of an array of individual four color binary combination code SML monofilament ID tag spectral emitter embodiments available from the emitters of FIG. 3.

Referring to FIG. 4, each tag support 403 formed from the preceding transection and removal process is distinct from each other, and thus generate a distinct spectral code, that may be termed binary (because each individual support frame supports a distinct combination of each SML monofilament and thus each of the four possible wavelength emission bands is present or not present). The tag support structure 403 and bonded SML monofilament arrangement is sealed, alternatively by standard vacuum deposition, transparent polymer or glass, or spin casting means. After sealing, each individual ID tag is separated with a standard semiconductor scribing technique, such as diamond sawing or laser cleaving, and encapsulated in beads. They are each now a distinct SML electromagnetic spectrum emitter.

Figure 5:
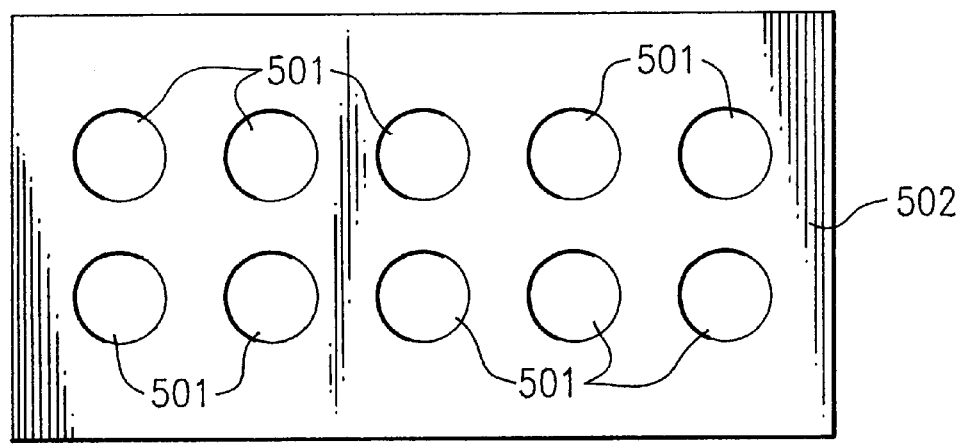
FIG. 5 is a top view of an exemplary array of a combination code ID tag spectral emitter fabricated as SML inks.

Referring to FIG. 5, 100–200 µm diameter SML dots 501 are deposited on transparent (such as glass) supports 502 by standard "ink jet" printing means. For a color code of 20 colors, 20 parallel print heads are attached to individual ink reservoirs. The pattern of ink emission is controlled by a programmed computer. Dots are deposited in a 5×2 array providing 10 distinct wavelength bands from an ensemble of 20 possible colors. The SML dots 501 are next sealed by means similar to those used to seal SML monofilament-based ID tag structures. After sealing, each tag is encapsulated and bonded to the molecular growth matrix.

Cast films are often composed of dye molecules embedded in a methylmethacrylate film. Such films are described in Balachandran, et al Applied Optics 35, p. 640–643 (1996). These films may be lithographically patterned. Thus, using multiple microlithographic imaging steps well known to those skilled in the art, arrays of separate laser paint regions, may be fabricated. The deposition process is as follows: Spin coat a distinct SML on a transparent substrate such as glass. Expose the transparent substrate with UV light through a mask. Develop away the exposed areas of the file on the exposed substrate, leaving behind 100–200 µm squares of SML. Then repeat this process the number of times required to fill in the entire transparent substrate, each time with a distinct SML spin coat on a region of the substrate. After completion of the deposition process, the substrate is coated with either glass, polyimide or plastic such as polystyrene, by methods known to those skilled in the state of the art. After coating, the wafer is sliced into 500–1500 µm tags, each comprising a distinct combination of SML emitter. After sealing, each tag is encapsulated and bonded to the molecular growth matrix.

Figure 6:
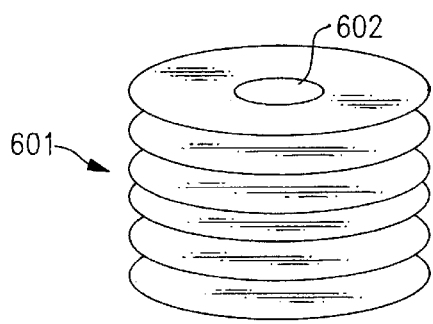
FIG. 6 is a top/side view of an exemplary of a combination code ID tag spectral emitter fabricated as SML rings enclosing a post.

Referring to FIG. 6, SML regions are fabricated in the form of 500–1000 µm diameter rings 601. The rings are fabricated by conventional molding, stamping from a sheet, or lithographic exposure. Here, an entire plastic cast sheet of one SML is fabricated into rings. Then tags are assembled by machine by placing a series of rings over 200–500 µm mounting posts 602, the mounting posts either on a planar substrate or from a spool of metal, or alternatively, a plastic filament. The mounting 602 post may be clear or formed from a scattering matrix, to facilitate photopumping of the tag at any orientation, or alternatively to facilitate radiate non-directional scattering of the spectral emission. Individual rings are looped over the post 602 either manually or robotically under computer control. Stacked rings are then encapsulated with alternatively a transparent plastic or glass coating and are ready for use as beads. This embodiment is inexpensive to manufacture, affords flexibility in photopumping because of the geometry of the discs, and is inexpensive to fabricate because of the relatively large size of each ring (500–1,000 µm diameter), and post (200–500 µm). SML regions fabricated as rings as herein described is the preferred embodiment of the spectral emitter of this invention.

Figure 7:
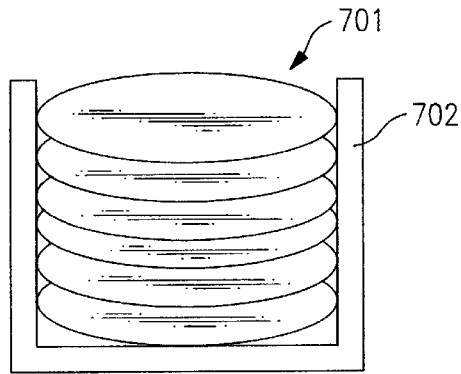
FIG. 7 is a top/side view of an exemplary of a combination code tag spectral emitter fabricated as disks enclosed in a transparent container.

Referring to FIG. 7, individual SML material shaped alternatively as a ring, or a disc 701 can be placed in transparent containers 702 and sealed to embody an ID tag. Spectrally Narrowed LED Array Combination Tagging Systems An LED array is another preferred embodiment for a combination coding tag.

The disadvantage of traditional LED light sources as frequency encoding devices, compared to lasers, relates primarily to their broad spectral emission or 50–100 nm bandwidth. This broad band makes it difficult to define the 20–40 distinguishable colors required to define a good combination code. This is the same problem that disadvantages using fluorescent molecules in spectral codes. However, recently a method has been described that allows significant narrowing of the emission wavelength from LEDs and fluorescent molecules, and in addition allows tunability of the emitted wavelength band. The method involves placing the emitting species inside a resonant microcavity, of dimensions on the order of the wavelength of the emitted light. (Yokoyama, Science 256, p. 66, (1992)).

The theory of quantum electrodynamics predicts that spontaneous emission is actually stimulated emission caused by the zero point energy fluctuation of the vacuum. It has recently been shown that if an emitting species is placed inside a highly reflective cavity, of size on the order of the wavelength of emission, and if the cavity diameter is chosen such that the cavity supports resonant modes that include only spectrally narrow regions in the full fluorescent bandwidth of the emitting species, then the spontaneous emission of the species outside the resonant region is substantially suppressed, while emission at the resonance frequency is substantially enhanced. Enhancement of the efficiency of emission at the resonant wavelength is true only if the emission spectrum is homogeneously broadened, i.e. the bandwidth breadth is caused by processes (such as vibration) that allow molecules to sample all energy and spatial configurations, and that result in light emission within a specie's emission bandwidth.

Microcavity concepts are used to make frequency narrowed LEDs. The first Resonant Cavity Light Emitting Diode (RCLED) was demonstrated by Schubert et. al. Appl. Phys. Lett., 61, p. 2287 (1992), who designed a conventional LED placed in a High Q optical cavity. The optical cavity enhanced the spontaneous emission at its resonant wavelength by as much as a factor of 10. Lott et al. Electron Lett. 29, p. 328 (1993) demonstrated red RCLEDs fabricated from AlInGaP heterostructures grown on GaAs substrates. Devices incorporating AlAs/AlgaAs quarter wave mirrors and an InGaP quantum well surrounded by InGaAlP barriers emitted at 665 nm with linewidths as sharp as 0.9 nm, a factor of 19 better than a comparable conventional LED. An organic light emitting device (OLED), a form of LED, RCLED has been reported by Dodabalapur et al. to emit simultaneously at three discrete wavelengths though the use of a multi-mode Fabry-Perot cavity. Dodabalapur et al. Appl. Phys. Lett., 65, p. 2308 (1994).

RCLED array light sources can be fabricated from many materials. Two attractive choices are Gallium Arsenide (GaAs), and its alloys, and Silicon. GaAs LEDs are the most common and efficient LED structures presently in use. Silicon bandgap LEDs emitting at 1.1 eV and visible LEDs have recently been demonstrated. Both Crystalline Silicon and GaAs form efficient photoelectric cells. Therefore, both materials can be configured with arrays of LEDs for emission. GaAs is advantaged as a material choice because of its good thermal stability. Silicon is useful because of its widespread use in solar cells and integrated circuit manufacture.

As stated above, the bandwidth of a GaAs RCLED may be as narrow as 1 nm. However it is advantaged to separate encoding frequency bands by at least 4 nm to simplify the design of the optical spectrometer used by a terminal apparatus to collect the bead emission spectral components Because the full emission bandwidth of a single configuration of a GaAs alloy LED emitting in the infrared may be from 0.05–0.1 eV or 50–100 nm, it is advantaged to use 1–2 non-overlapping bandwidth LED alloys to cover a full set of encoding frequencies. Twenty five to thirty frequency wavelength bands are required for the entire combination code. Five to ten RCLED structures are used to define the encoding frequency components for each bead. A GaAs chip is configured in a similar manner to that of an OLED array.

Because OLEDs emit over the spectral range of 400–700 nanometers, and RCLEDs have bandwidths substantially less that 10 nanometers for high Q cavities, 20–30 different color bands are easily defined. Cavities are deposited during tag fabrication by thin film techniques well known to those skilled in the art. Six to eight RCLEDs may easily be incorporated in a single tag (though this number varies with each particular embodiment). Cavity tuning is accomplished by deposition of a spacer layer of appropriate thickness as described in Dodabalapur et al. These investigators used $Si_xN_y$. Twenty different spacer thicknesses can be laid down in only 5 deposition steps. The method for doing so is described in the Vertical Emitting Semiconductor Laser Array embodiment described presently.

For use in combination coding applications the key element is the reproducibility of the spectral narrow band pass light emission from the microcavity. In the electroluminescent microcavity, one reflector is a distributed Bragg reflector and the other reflector is a metal reflector of high reflectivity which also serves as an electrode. The emitting region can be comprised alternatively of OLED material, GaAs and its alloys, or porous silicon. The spacer material can be silicon nitride.

Figure 8:
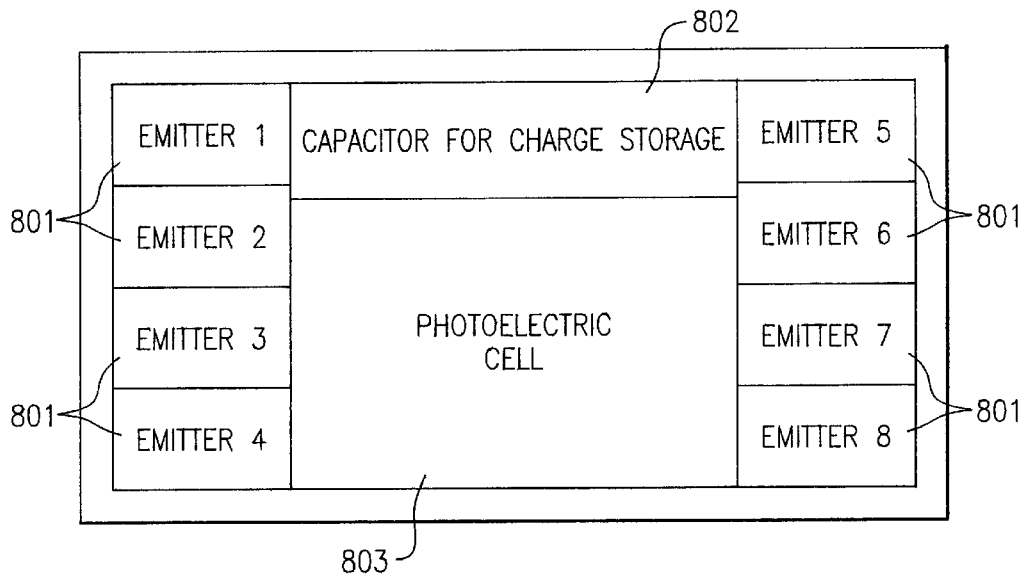
FIG. 8 is a schematic of a nominal LED combination code spectral emitter ID tag layout.

Referring to FIG. 8, an LED based combination code emitter layout is portrayed without wavelength band narrowing structures. Eight LED emitters 801 providing eight distinct emission wavelength bands, supported on a substrate with a capacitor for charge storage 802, and a photoelectric cell 803 for energy absorption. The fabrication of such an emitter has already been described in the section of this patent addressing embodiment of a bead with an electrical circuit, and referenced in FIG. 2. The light source chosen may be a white light Organic LED (as described in U.S. Pat. No. 5,405,709), or a combination of OLEDs. If the LED is fabricated on a glass substrate. If a silicon substrate is chosen silicon or OLED light emitters are used. Gallium Arsenside (GaAs) alloy LEDs are require fabrication on GaAs. Arrays of LEDs are chosen to emit multiple colors.

An OLED array is powered by amorphous silicon photoelectric power cells because the preferred embodiment is fabricated on glass. (A crystalline silicon photoelectric cell is recommended if the array is fabricated on a silicon wafer). Under illumination by an external photon source, such as a terminal apparatus, the OLEDs are powered up and resonantly emit a distinct color for each OLED. The emitted spectrum is read with an optical spectrometer, from light collected by an integrating sphere, lens or mirror placed around, or near to the bead. Readout is accomplished in less than 10 milliseconds, with verification, and rereading (if required), occurring within 50 milliseconds.

Referring to FIG. 9, a plurality of separate LED emitter medium, here shown as 901*a,* 901*b,* 901*c,* 901*d,* 901*e,* and 901*f;* are each disposed between a Bragg reflector, shown respectively as 902*a,* 902*b,* 902*c,* 902*d,* 902*e,* and 902*f;* and a spacer, shown respectively as 903*a,* 903*b,* 903*c,* 903*d,* 903*e,* and 903*f.* On the other side of the spacer is a metal reflector, shown respectively as 904a, 904b, 904c, 904d, 904e, and 904f. The dimensions of each spacer are distinct, and thus the spectral emission of each LED is narrowed to a distinct wavelength band. Interposed in each cavity is a semitransparent electrode 907a, 907b, 907c, 907d, 907e, and 907f respectively. These electrodes 907a–907f completes the current paths through the emitting medium. Surrounding each LED-microcavity combination is a scattering medium 905 that enables the emitted light to radiate non-directionally. In electrical communication with the LED emitting medium is a photoelectric cell 906 that absorbs light from an external source and converts that light into an electric power that it supplies to the LED emitting medium.

Less preferentially the frequency of emission can also be defined by thin film filters deposited over the top of an LED array. These filters may have a bandwidth of 5–20 nanometers, depending on the fabrication technology (see for example Laser Focus World, March, pp. 111–115 (1997). Narrow bandpass filters in the 5–15 nanometer range are fabricated from either Fabry-Perot Etalon structures, or multilayer dielectric stacks. Multi-cavity Fabry-Perot filters are utilized for 5 nm bandpass, and multilayer stacks are utilized in less demanding 10–15 nm bandpass filters. The wavelength of transmission is tuned by changing the thickness of the Etalon cavity or the thickness of the dielectric layers. These kind of filters work well when the angle of incidence relative to the incident radiation is less than 30 degrees from the normal to the surface (Oriel, Optics and Filters Catalog, III (1990)). The LED electroluminescent electron-hole recombination radiation process intrinsically emits radiation incoherently, that is all directions. To limit the angle of the LED radiation incident on the overlying thin film filter, a low refractive index layer may be interposed between the emitter and filter. Due to Snell's Law, light incident on the interface between a high refractive index ($n_2$) layer and a low refractive index ($n_1$) layer will not propagate past the boundary if the angle of incidence is greater than the critical angle ($\theta_c$) defined by:

$$\theta_c = \sin^{-1}(n_1/n_2)$$

If $n_1=1.5$ and $n_2=3.0$ than $\theta_c=30$ degrees. This is an adequate angle of incidence restriction for this application. However, because multilayers do not enhance the spectral emission efficiency of the source at transmission resonance, as in the Case of RCLED structures, they are not as advantaged for incorporate into a frequency code.

Referring to FIG. 10, each LED, shown as LEDs 1001a, 1001b, 1001c, 1001d, 1001e, and 1001f, have a low index of refraction layer 1002 disposed on top of each LED to lower the angle of incidence of the light emitted by each LED relative to Fabry-Perot filters disposed above that layer. The Fabry-Perot filters, shown as 1003a, 1003b, 1003c, 1003d, 1003e, and 1003f, wherein filter 1003a is associated with LED 1001a, filter 1003b is associated with LED 901b, etc. Disposed within each Fabry Perot filter is an Etalon cavity, shown here as 1004a, 1004b, 1004c, 1004d, 1004e, and 1004f, for each of the LEDS 1001a–1001f. The wavelength of transmission of each Fabry Perot structure is dependent upon the thickness of the Etalon cavity. A distinct thickness for each cavity thus implies a distinct emission wavelength for each LED based spectrum emitter. Each LED-refractive layer-Fabry-Perot filter is surrounded by a scattering medium 1005 to scatter the emitted light. The LEDs themselves are powered by a photoelectric cell 1006 that is in electrical communication with the LEDs and absorbs light from an external source and converts that light into an electric power that it supplies to each LED.

Referring to FIG. 11, each LED, shown as LEDS 1101a, 1101b, 1101c, 1101d, 1101e, and 1101f, have a low index of refraction layer 1102 disposed on top of each LED to lower the angle of incidence of the emitted by each LED relative to multilayer filters disposed above the refraction layer 1102, each LED associated with a distinct filter, shown here as filters 103a, 1103b, 1103c, 1103d, 1103e, and 1103f. Each filter distinctly narrows the electromagnetic emission spectrum of each LED. Each LED-refractive layer-filter is surrounded by a scattering medium 1104 to scatter the emitted light. The LEDs themselves are powered by a photoelectric cell 1105 that is in electrical communication with the LEDs and absorbs light from an external source and converts that light into an electric power that it supplies to each LED.

Microcavity Fluorescence Microcavity Arrays

Fluorescent molecules in resonant microcavities may be optically pumped and emit narrowband light via radiation mode controlled photoluminescence. Fluorescent molecules include organic metal chelates, organic dyes, and poly (p-phenylenevinylene) (PPV) (Yokoyama, Science 256, p. 66 (1992). Photoluminescent (PL) microcavities may be configured in arrays that embody tags for combinatorial beads. Such cavities emit light by either spontaneous emission (as described by Gruner et al J. Appl. Phys. 80, p. 207–215 (Jul. 1, 1996), and Dodabalapur et. al., Appl. Phys. Lett., 64, p. 2486–2488 (1994), by stimulated emission, or by lasing (as shown by Tessler et al., Nature, 382, p. 695–695). Whether a microcavity emits by spontaneous emission or stimulated emission is a function of the level of photopumping stimulation, the optical gain in the medium, and the losses from the cavity.

Figure 12:
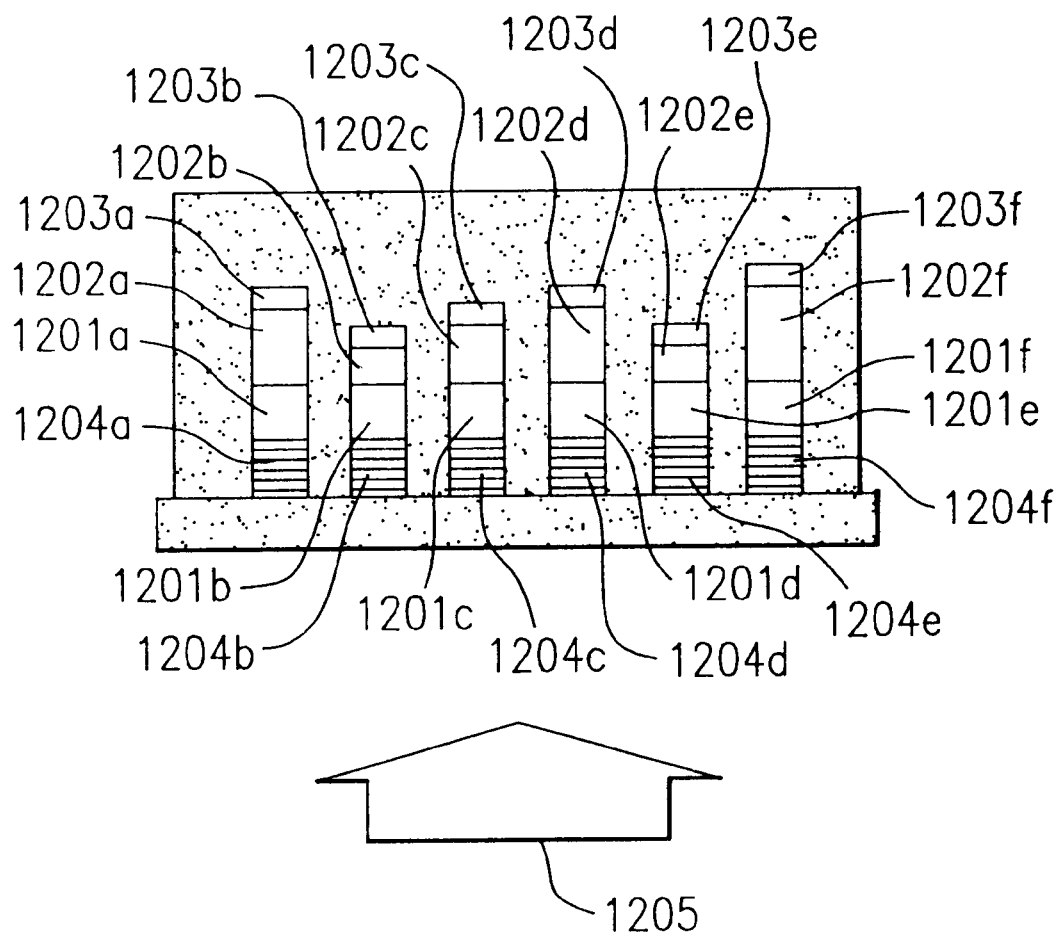
FIG. 12 is a side view of a schematic of an exemplary fluorescent emitter array wherein each fluorescent emitter is surrounded by a microcavity to narrow the wavelength band of the emitted light.
Figure 15:
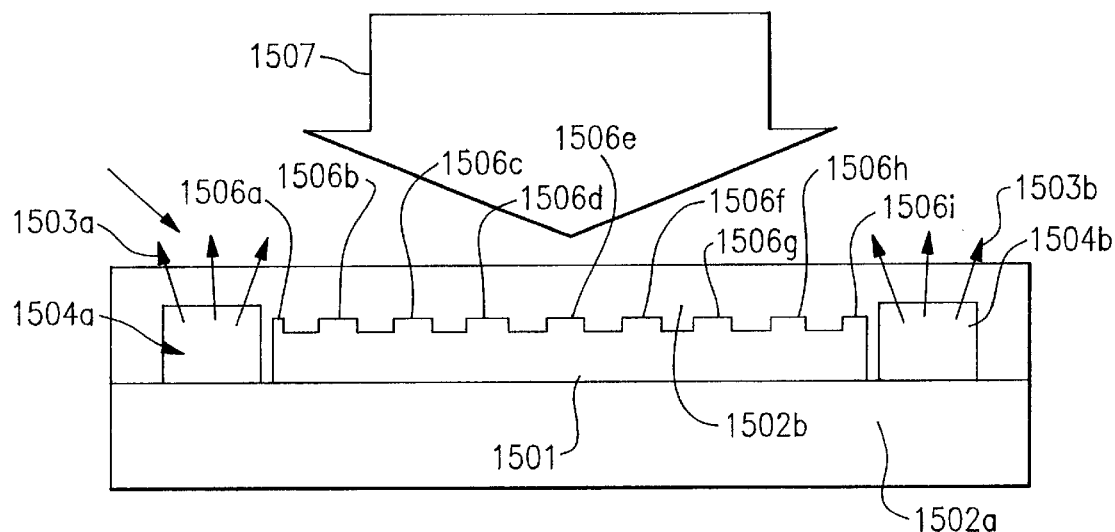
FIG. 15 is a side view of a schematic of an exemplary of a Planar Waveguide Luminescent Polymer Laser electromagnetic spectrum emitter with Distributed Feedback.

For use in combination coding applications the key element is the reproducibility of the spectral narrow bandpass light emission from the microcavity. A typical resonant cavity PL structure is shown in FIG. 12. Referring to FIG. 15, fluorescent emitting media 1201a, 1201b, 1201c, 1201d, 1201e, and 1201f, are each below a resonant cavity spacer 1202a, 1202b, 1202c, 1202d, 1202e, and 1202f respectively on top of the fluorescent emitting media, and a metal reflector 1203a, 1203b, 1203c, 1203d, 1203e, and 1203f respectively, of high reflectivity. Below each emitter is a distributed Bragg reflector 1204a, 1204b, 1204c, 1204d, 1204e, and 1204f respectively. The distributed Bragg reflector side of the fluorescent emitting media is configured to allow photo pumping of the fluorescent material outside the bandpass of the cavity, as well as providing high reflectivity over the entire fluorescence bandwidth of the molecules in the microcavity. Each resonant cavity spacer 1202a–1202f is of a distinct dimension, thus resonating a distinct wavelength band, and producing an emission for each emitter in a distinct wavelength band. The photo pump light 1205 is from a source external to the emitter and is preferably provided by a terminal apparatus derived laser. The laser emits a 1 to 10 nanosecond pulse of photons, each photon being more energetic than the emitted fluorescent photons. In one embodiment, emission is stimulated by a standard one photon fluorescent process that results in emission Stokes shifted light emissions. Alternatively, the laser may emit a picosecond or femtosecond pulse of light, where the pump photons are significantly less energetic than the fluorescent photons. In this case, fluorescence takes place via a nonlinear optical two, or more photon excitation process as described in U.S. Pat. No. 5,034,613.

Optically Pumped Waveguide, Grating Mode Controlled and Micro Distributed Feedback Laser Arrays Recently it has been demonstrated that planar waveguide luminescent polymers can act as lasers when they are photo pumped. (Hide, et al., Laser focus World, p. 151–156 (May 1997)). Semiconductor luminescent polymers have been shown to lasers from 420–640 nanometers, a stokes shifted emission when pumped with light from 355–532 nanometers. (Hide et al., Science, 273, p. 1833–1836 (1996)). Dye molecules embedded in plastic can also be cast as thin films to act as lasing waveguide structures. Laser dyes emit from 400–1200 nm when photopumped from 355–900 nm.

Semiconductor polymer films have a refractive index from 1.6–2.0 depending on the particular material. When a thin film of the material of from 0.25–4 microns thick is bounded on each side by a lower index material such as glass (n=1.5), or air (n=1.0), the layer functions as a dielectric waveguide. In this configuration photo pumped lasers are caused to lase by the process of amplified spontaneous emission (ASE). In ASE, spectral narrowing of the fluorescent bandwidth occurs, and light emission radiates from the film.

Figure 13:
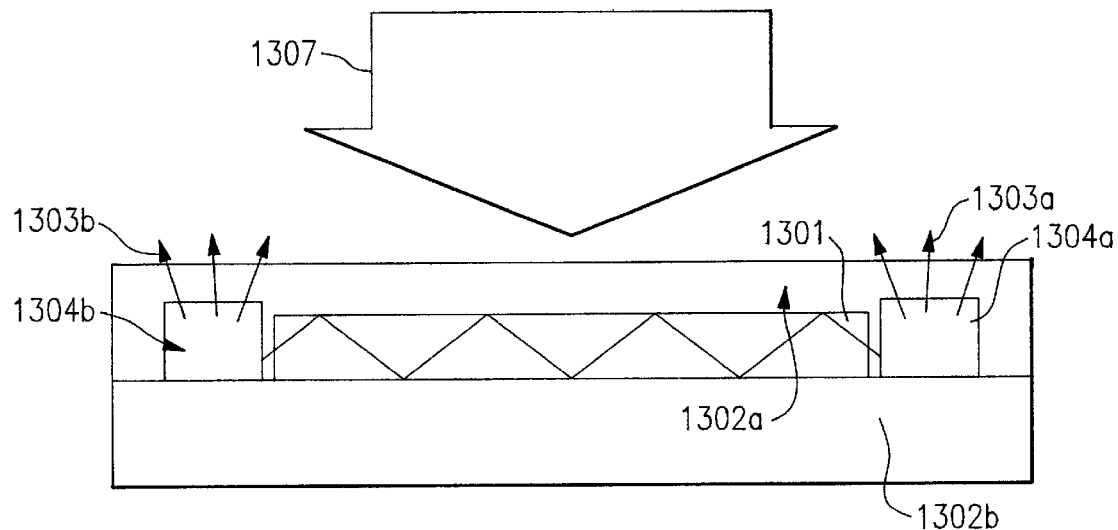
FIG. 13 is a top view of a schematic of an exemplary Planar Waveguide Luminescent Polymer Laser electromagnetic spectrum emitter.

Referring to FIG. 13, a lasing medium 1301 functioning as a waveguide is bounded on each side by material layers of a lower refractive index, 1302a and 1302b, and is pumped with light 1307 from an external source. Lasing occurs near the peak of the fluorescent and spectral gain curve. Arrays of ASE lasers are configured out of different polymer or plastic impregnated with dyes Tuning of the wavelength emission is achieved by use of distinct polymers or dye molecules, changing the ratio of copolymer monomeric units or in the case of organic dyes by altering the pH of the plastic matrix changing the states of ionization, or local fields of the materials and hence the emission spectrum (as is done with SML systems). Thus, each emitter emits a distinct wavelength band. The direction of ASE emission is controlled by the aspect ratio of the lasing medium. The laser light 1303a and 1303b passes out of the lasing medium and through scattering medium 1304a and 1304b, whereby the light is directionally scattered.

Lower threshold operation, narrower bandwidth emission, and finer control of the emitted frequency of a planer waveguide laser are achieved by providing cavity mode selecting feedback into the lasing medium. In bead electromagnetic spectral emitter applications, it is difficult to fabricate a mirror structure about a planar waveguide. It is preferable to use grating feedback where the gratings are arrayed on each side of the lasing medium, or in the lasing medium itself to embody a distributed feedback laser (DFL), as described in Yariv, Quantum electronics, $3^{rd}$ Ed. John Wiley & Sons, New York p. 600–623. The grating period $\Lambda$ is defined by:

$$\Lambda = l\pi/\beta_0$$

where $l$ is the an integer, and $\beta_0$ is the propagation constant near the Bragg value of:

$$\beta_0 = (\omega/c)n_{eff}$$

where c is the speed of light, $n_{eff}$ is the effective refractive index of the material, and $\omega$ is the angular frequency of the lasing radiation. For DFL applications, grating spacings are in the range of 0.2–1.0 microns. Patterning is be accomplished by multiple forms of conventional optical microlithography, (described presently). DFL cavities can be well under 1 mm in length and lasing wavelength can be controlled to as little as 1 nanometer. Use of DFL for bead electromagnetic spectrum emitters minimizes the quantity of distinct lasing media that must be used to constitute an electromagnetic spectrum of a combination code because the wavelength band of the lasing emission is not controlled by the peak of the fluorescence curve, but rather by the grating period. In addition, the narrower emission bandwidth of DFLs allow many more frequencies to be used in the set of frequencies that define the code. More than 50 frequency components may be obtained with a spacing of 4 nm between components.

A preferred fabrication sequence of a DFL polymer laser is described. First, a transparent material with a low index of refraction such as a glass substrate is coated with photoresist. The photoresist is exposed using a conventional lithographic process that exposes at a resolution of 0.4 microns period. An example of a lithographic process is the double grating holographic process described in Smith et al., Applied Optics 31, p. 4540, 1992, and the holographic lithography system HLS System 1000 commercially available from Holographic Lithography Systems, Inc., Bedford, Mass. The double grating approach has been used to make gratings with periods as small as 0.1 micron. After exposure, the photoresist is developed, and the grating pattern is revealed. The grating pattern is transferred into the glass via a standard reactive Ion etch step. The glass is then cleaned, and alternatively a thin layer of semiconducting luminescent polymer or a dye impregnated plastic is spin coated on the substrate. The above encapsulation structure is completed by spin coating the photoluminescent layer with a transparent low refractive index plastic or glass. Individual ribbons of DFLs are then integrated into a single electromagnetic spectrum emitter.

Alternatively, the holographic lithography step may be replaced by a microlithographic pattern transfer of multiple grating structures written by an electron beam system onto an optical photomask. The microlithographic exposure tool used for this process is a conventional high resolution contact printer as sold by Canon, or Karl Seuss, or a conventional optical projection microlithographic stepper system used to make integrated circuits, as sold by ASM lithography, Canon, Nikon, etc. Stepper systems that print grating periods of 0.5 microns are commonly available. Regular arrays that are substantially smaller, may be printed with the technique of phase shifting masks. Using a mask transfer technique, all the DFLs required for each electromagnetic spectrum emitter are fabricated on a single substrate, and separated by a substrate dicing procedure.

Figure 14:
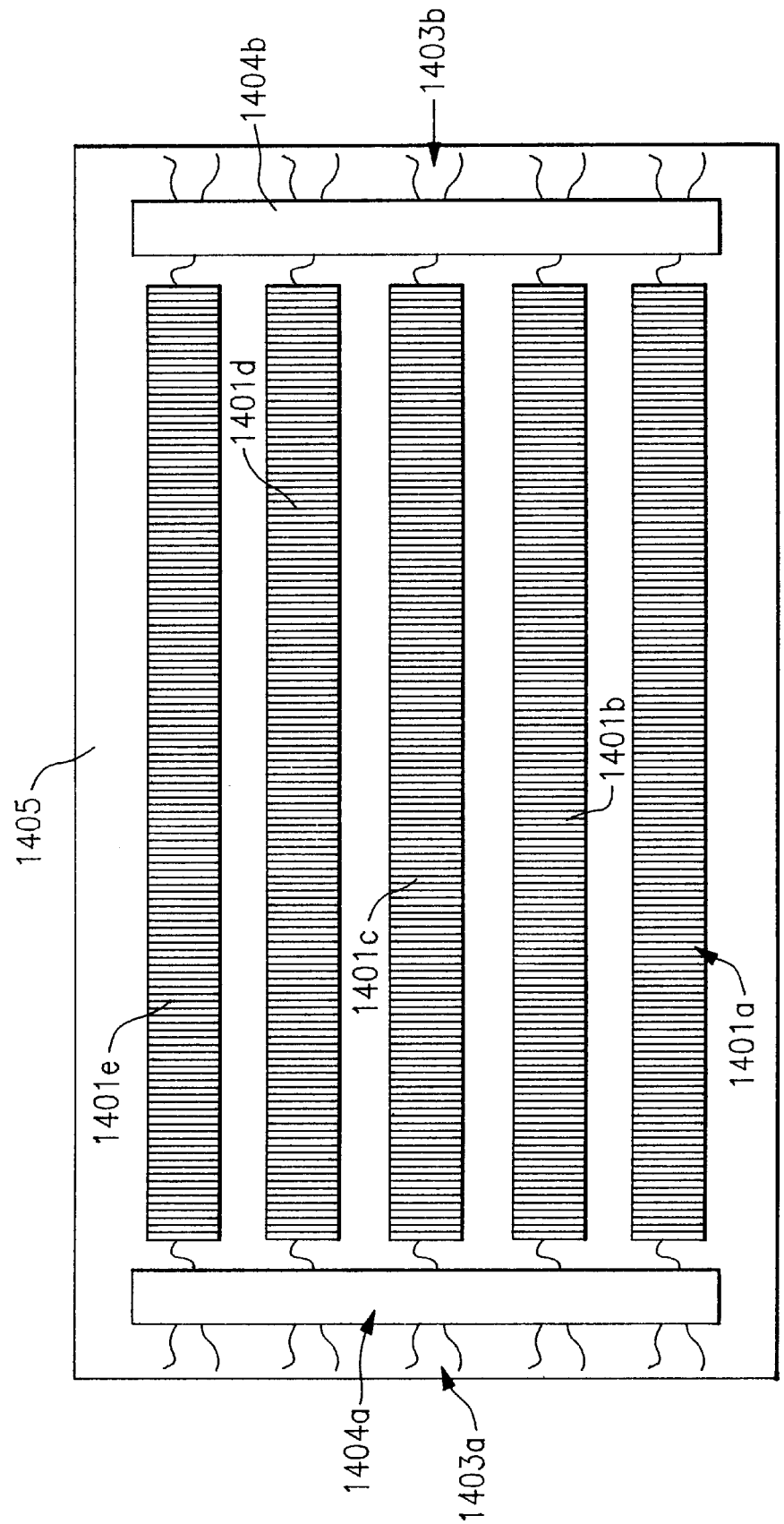
FIG. 14 is a top view of a schematic of an exemplary Planar Waveguide Luminescent Polymer Laser electromagnetic spectrum emitter with Distributed Feedback that tunes the emission wavelength band.
Figure 16:
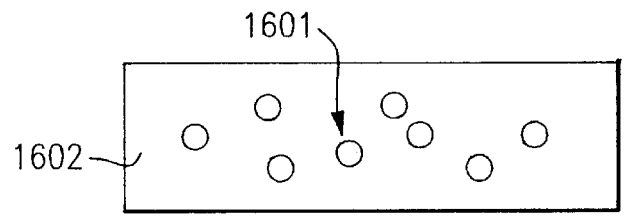
FIG. 16 is a side view of a schematic of separate Raman emitters enclosed in a resonant spherical microcavity packed in a low index matrix, where each Raman emitter radiates a distinct wavelength band.

Referring to FIG. 14, a linear array of DFLs including feedback grates, of size 10×50×600 microns 1401a, 1401b, 1401c, 1401d, and 1401e, functioning as a waveguide, are arrayed on a substrate 1405, and pumped with light (not shown) from an external source. Each array is bounded on each side by material layers of a lower refractive index (not shown). The laser light 1403a and 1403b passes out of the lasing medium and through a reflective, dispersive, or scattering medium 1404a, 1404b, is provided at the output of the array to enable sensing of the emitted spectrum from all directions. The lasing media are embedded in low n materials to make up the waveguide structures.

Referring to FIG. 15, a DFL 1501, functioning as a waveguide, is bounded on each side by material layers of a lower refractive index, 1502a and 1502b, and pumped with light 1507 from an external source. Narrowing of the wavelength emission is performed by feedback gratings including a relief structure of bars 1506a, 1506b, 1506c, 1506d, 1506e, 1506f, 1506g, 1506h, 1506i, running across the lateral axis of the DFL. The laser light 1503a and 1503b passes out of the lasing medium and through a reflective, dispersive, or scattering medium 1504a and 1504b, provided at the output of the array to enable sensing of the emitted spectrum from all directions.

Optically Pumped Resonance Raman and Spherical Microcavity Tag Embodiments

Raman Spectroscopy is most commonly used as a tool for studying the vibrational energy levels of molecules, and lattice branch vibrations of crystals. Typically a sample is irradiated with a narrow band optical wave. A spectral analysis of the scattered light reveals the existence of frequencies that are shifted down by increments equal to the vibrational frequencies of the irradiated material. This type of scattering is referred to as Stokes scattering. Frequencies upshifted to equal the sum of the incident wave frequency and the vibrational frequencies are also present in the scattered radiation. This is referred to as anti-Stokes scattering and its intensity is usually orders of magnitude below that of the Stokes scattering. There are many vibronic levels in different chemical bonds, from a wide variety of molecules that can be used to make up a frequency code. However, ordinary Stokes scattering is an inefficient process, and is therefore not suitable to form the basis of an embodiment for an ensemble of frequencies to make up a frequency code. Furthermore it is possible that the Raman emission from the growth matrix and the oligomeric compound attached to the matrix may be confused with Raman encoded signals.

There are two methods of substantially enhancing Raman signal levels. These are the processes of resonance Raman scattering and Stimulated Raman Scattering (see Yariv, Quantum Electronics $3^{rd}$ Ed. John Wiley & Sons, New York, p. 453–475 (1987)). A resonance Raman scattering process provides a stimulus light of a frequency within the electronic absorption band of the molecule. This process increases the signal level several orders of magnitude and is used to form the basis of a series of compounds to form a combination frequency code.

Stimulated Raman scattering is a non-linear optical process, and causes light to be added to the Stokes shifted field by a stimulated emission process, which is similar to the process used to produce laser light. Normally the gain length required to result in significant gain is measured in centimeters or longer, and optical stimulus fields are often of quite high intensity. Therefore, stimulated Raman scattering is not readily useful for bead encoding applications. However, if the Raman medium is placed inside a 2–50 micron diameter spherical microcavity, intense stimulated Raman radiation is emitted at modest laser illumination as has been shown by Lin and Campillo. (Phys. Rev. Lett. 73, p. 2440–2443). A spherical microcavity has the characteristics of large mode density enhancements on resonance ($>10^4$ and cavity Q's as high as $2\times10^8$). Non-linear gain enhancement may be 100 times that observed in bulk media. Sphere diameter variation is used to tune the microsphere Q to the specific Raman lines to be enhanced.

Referring to FIG. 16, 5–20 micron diameter spherical microcavities 1601a, 1601b, 1601c, 1601d, 1601e, 1601f, 1601g, and 1601h shown as 8 separate microcavities, enclose by encapsulation enclose Raman emitting materials. Each spherical microcavity enclosed Raman emitting material is an emitter of a distinct wavelength band as a function of the diameter of each microcavity. The 5–20 micron diameter range provides 40 discrete vibronic levels, and thus 40 distinct spectral code wavelength bands. The Microcavity boundary is either part of the gain medium, as in the case of dye molecules immobilized in plastic, or formed from glass with a thin metalized coating. The thin metalized coating provides the refractive index mismatch between the cavity boundary and the surrounding medium 102, to enable high Q operation. The metalized coating is deposited in a thin layer to allow pump light to excite the stimulated Raman process. The low index of refraction surrounding medium that the individual Raman emitting microcavities are packed may be an aerogel or in the case of metalized particles, a plastic matrix.

Vertical Emitting Semiconductor Laser Arrays

Figure 17:
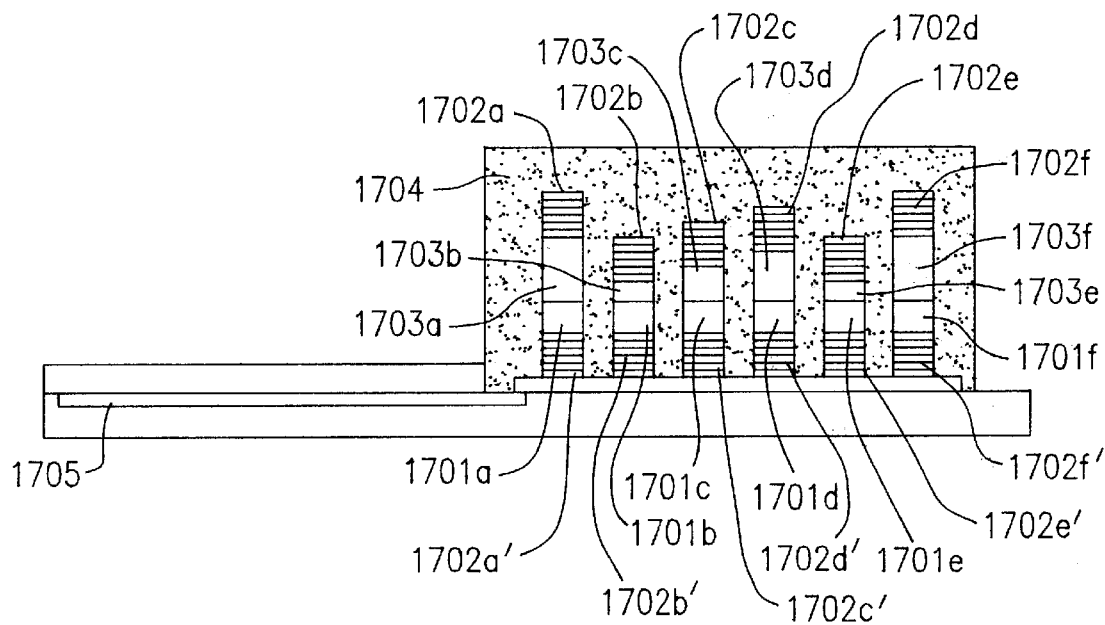
FIG. 17 is a side view schematic of an array of semiconductor lasers, each in a vertical cavity, known as a Vertical Cavity Surface Emitting Lasers, for emitting spectrum of distinct wavelength bands.

Semiconductor lasers have traditionally been fabricated in a waveguide geometry, where the emission of light occurs along the plane of the substrate upon which the device is fabricated. This class of lasers is referred to as edge emitting lasers (EEL). Tuning the emission light wavelength entails varying the dimension of a surrounding resonant cavity or alternatively varying the lasing medium alloy composition. High density arrays of semiconductor lasers are made preferentially in a Vertical Cavity geometry and are called Vertical Cavity Surface-Emitting Laser (VCSEL). Referring to FIG. 17, a VCSEL array is composed of separate lasing medium 1701a, 1701b, 1701c, 1701d, 1701e, and 1701f, each lasing medium sandwiched between two distributed Bragg reflector stacks 1702a, 1702a', 1702b, 1702b'. 1702c, 1702c'. 1702d, 1702d', 1702e, 1702e', 1702f, and 1702f', where Bragg reflector stacks 1702a and 1702a' are sandwiched around lasing medium 1701a, Bragg reflector stacks 1702b and 1702b' are sandwiched around lasing medium 1701b, etc. (Active Electronic Component handbook $2^{nd}$ Ed. Harper and Jones, McGraw, New York, p. 9.57 (1996)).

Respective resonant cavities 1703a, 1703b, 1703c, 1703d, 1703e, and 1703f is each between a Bragg reflector and the lasing medium. Each cavity space is distinct, a ¼ wavelength thick, thus emitting a distinct wavelength band. The array is surrounded by a scattering medium 1704 and powered by a photoelectric cell 1705 that absorbs light from an external source and converts that light to an electrical current that it supplies to each lasing emitter. VCSELs may be 6–8 microns in diameter (or smaller) with a vertical cavity length of 5 microns. The vertical cavity geometry is ideal for configuring as ID tags. They provide the smallest embodiment of a spectrally narrowed ID tag array. Their primary disadvantage is that of VCSEL fabrication requires sophisticated process technology that includes molecular beam epitaxy. VCSELs are traditionally fabricated as multi-quantum well structures in GaAs. To achieve each of the distinct lasing wavelengths required for a combinatorial chemistry combination code, the cavity length of each laser must be distinct. At least 20 different emission bands are contemplated for the spectral codes disclosed here. Laser emission wavelength may be tuned by depositing a resonant cavity spacer material such as $Si_xN_y$.

Using the novel deposition strategy described here, at least part of the fabrication complexity of making arrays of VCSELs that emit at different wavelength bands is reduced. Twenty distinct thicknesses can be deposited in 5 separate deposition steps. The strategy is to provide a deposition thickness at each step equal to a bit in a binary representation of the number of thickness' required. For example, if the required spacer thickness is to vary from 0–500 nm, with 25 steps, a unit of one thickness equals 20 nanometers. In binary notation, "25" is 11001, and the deposition steps to deposit 500 nm of material are: 320 nm, 160 nm, and 20 nm, from a set of 5 deposition thicknesses: 320 nm, 160 nm, 80 nm, 40 nm, and 20 nm. The specific VCSEL that receives a spacer deposition increment is defined by a microlithography exposure and development step.

An array of 5–10 VCSELs may be deposited in less than a 75×75 micron array, and with an auxiliary photocell for power makes up an extremely compact ID tag. Directionality of the emitted radiation is spoiled by placing a scattering medium above the output coupling reflectors.

Permutation Spectral Emitter Embodiments

Permutation frequency encoded tag systems require all the capabilities of combination systems, with the additional capability of time sequence encoding of the frequencies of emission. Thus, in a sense they represent a discrete frequency modulation (FM) system of output. Time sequencing of output frequencies requires the intervention of a sequencing device between a triggering signal and the output pulses of electromagnetic radiation frequency encoded information. That sequencing device is most appropriately an electrical circuit.

A major goal of encoded tag design is a bead of at most 2 mm diameter. Therefore, any included device must accordingly be small to maintain a 2 mm diameter design goal. Thus, any included electrical circuit must to be small and consequently simple. Accordingly, it is desirable to not include in the electrical circuit a programmable apparatus—to the extent that the electrical circuit must store a sequential code, the information is incorporated into a chip during fabrication, as a defined sequential logic structure, or as predefined biases in the transistors that make up code storage registers, rather than into programmable digital circuitry.

Bead transport rates through the recording device dictate at least two specific system requirements from the list presented in the Background Section. These are: 1) the requirement for high resolution spatial localization of the beads during the identification and sorting steps, and 2) high speed readout. Specifically high spatial localization requires localization to better than 3 mm in the direction of bead flow. High speed readout requires readout times of less than 50 msec. per bead, or the requirement that beads be identified and catalogued at rates greater than $10^5$ beads per hour. Requirements for spatial localization and small size both mandate off-chip optical triggering and/or powering of the bead tag during readout. Optical power sources can be focused to a resolution much greater than the desired spatial resolution with high optical power fluence. Additionally, optical signals are easily pulsed at high speed to form signals that act as off-bead clocking, or toggle systems to sequentially strobe out encoded ID information. The encoded information requires a sequence of from 6–30 pulses of frequency signals (depending on the number of possible encoding frequencies). Therefore, the toggling should be provided at a rate of 10–100 Kilohertz to allow readout to occur in well under 50 milliseconds, or preferably in under 10 milliseconds.

Because an optically read ID tag does not require remote writing to memory, the chip of the electrical circuit does not require fabrication on a silicon substrate. Thus, an embodiment fabricated on glass/silicon and two embodiments fabricated on Gallium Arsenide (GaAs) are presented.

GaAs Microchip Permutation Code Tagging Systems

The first preferred embodiment of an optical permutation encoding system is fabricated on a binary encoding tag on a GaAs substrate. GaAs is an advantaged material for the ID application for several reasons: 1) GaAs and GaAs alloy LED's are among the most efficient light emitting diode technologies. Emission efficiency is greater than 10%. In addition the bias electrical potential of the GaAs LED is 2–3 Volts, reducing the voltage requirement for on-bead photoelectric cells; and the drive current can be high, thus allowing each LED to be fabricated with very small diameters, thus conserving chip area; 2) GaAs p-n junction photoelectric cells produce greater than 1 Volt potentials. Thus, only 3–5 cells need to be cascaded in series to provide voltage for on-bead optical emitters and electronics, again conserving chip area; 3) The bandgap in GaAs is 1.45 eV. This allows the device to be powered and emit in the red and near infrared regions of the electromagnetic spectrum, minimizing any damage to the growing oligomeric compounds because organic molecules absorb poorly in this region of the electromagnetic spectrum. It is likely that GaAs chips enable the smallest beads and the highest thermal operating point of 250 degrees C., because of the large relative bandgap.

A figure of a permutation coding LED emitter chip has already been presented in FIG. 2. A GaAs LED permutation coding emitter requires a GaAs photoelectric cell, a charge storage capacitor, a GaAs photodiode, two GaAs LED's with separate thin film filtration, and simple digital switching circuitry and a register. The GaAs LEDs are incorporated into a substrate. It is simplest to provide independent frequency emission from the LEDs by using a broad band emitter structure, and then providing thin film filtration over the top of the junctions to select out separate spectral regions for encoding. The emission spectral half width for red and near infrared GaAs LEDs is greater than 50 nm. Two distinct frequency bands are provided by thin film filters placed over the top of the LEDs. It is advantaged to use two color emission to encode a binary code for ID tags rather than one color emission. Single color encoding requires that a binary zero be encoded either as a different intensity output signal than a binary one (discrete amplitude modulation), or as the absence of a signal. However, signal intensity may vary with orientation and the absence of a received signal can be caused by unusual misorientation, or malfunctioning, rather than a binary zero transmission. However, with two color encoding, there is less possibility of lost data, caused by bit frequency recognition errors. A 24 bit number can be encode $16.8 \times 10^6$ distinct codes. Signal fidelity can be checked by the implementation of one or more parity bits in the output code.

Clocking of the output stream is accomplished by toggling on and off an external clocking laser. The bit toggling is triggered by the leading or trailing edges of a toggling light state change. Power from the host laser system is provided before and after data transmission. If more power is needed to pulse an entire 24–26 bit stream, that power than can be stored in the on-chip capacitor, with the LED emissions pulsed out in packets.

An alternative embodiment of a GaAs tag uses a single LED emitter that may take the form of a dynamically tunable RCLED as described by M. C. Larson and J. S. Harris, IEEE Photonics Technology Letters, pp. 1267–1269 (1995). Here an electrostatically deformable membrane mirror is used to tune the cavity size and hence the emission frequency of the RCLED. The device is broadly tunable over 40 nm with spectral linewidths as narrow as 1.9 nm for operation near 950 nm. Therefore, this device allows up to 20 distinct frequency encoding bands that may be tuned and emitted sequentially from a single GaAs LED based electromagnetic spectrum emitter.

Glass Substrate Permutation Coding Tags

The ID Tag fabricated on glass includes amorphous silicon transistors for implementation of logic functions, amorphous alpha silicon photocells, and 2–4 different color OLED spectral emitters. Glass based chips are likely to be the cheapest to manufacture. Because the OLEDs are fabricated on glass, light can be emitted through the top and bottom of the ID Tag, if they are fabricated as a four layer OLED whose cathode is a thinned metal electrode over coated with transparent conducting indium tin oxide, as described by Bulovic, et al (Nature, 380, p.-29 (Mar. 7, 1996)). Alternatively, top emitting OLEDs can be used with a readout system fabricated with an integrating sphere to capture light emitted in almost any direction. A plurality of distinct color emitters are enable by use of distinct filters, or alternatively the selection of distinct choice OLED materials. Deposition of 10 nm interference filters below the emitters allows use of tens of color emitters, although this is not a likely coding requirement. Many color outputs are possible, because OLED devices can emit light across the visible spectrum, from 400–700 nm. For illustration, using two colors, a green emission from undoped Aluminum dihydroxyquinoline (Alq) and a red emission from doped dye DCM1 Alq (as described in Tang, VanSlyke and Chen, Appl. Phys. 65, #9, pp. 3610–3616.). This device operate in a manner similar to the GaAs chip described above.

Microwave Permutation Coding Tag

Non-optical permutation coding devices can be fabricated on GaAs, and use microwave frequency transmission codes. Single chip microwave system design is a rapidly maturing art driven by the requirements of mobile communications systems. High frequency systems are usually fabricated in GaAs substrates, although deep submicron silicon devices are also possible. For the ID tagging application, it is still important to trigger toggling frequency components, and power the tag optically to provide spatial localization of the chip during readout and sorting. The chip includes a small register to encode up to 24 distinct possible frequencies that the code includes. The register is toggled by the optical clocking pulses, and each frequency component is sequentially transmitted by the on-tag antenna. The microwave system required to enable the on bead ID tag must be tunable in discrete frequency steps. Choice of systems includes variable oscillators and frequency synthesizers and are reviewed in the Active Electronic Component Handbook $2^{nd}$ Ed., chapter 5. ID tag design is distinct from traditional FM system design because frequency is slewed in distinct steps, and transmission at a single frequency occurs over many frequency cycles. Therefore tracking time and settling problems are minimized. For the ID tag embodiment frequency synthesizers are preferred. Frequency synthesizers are derived from alternatively phase lacked loops (PPL) or direct digital synthesizers (DDS) which modulate the output frequency of alternatively a crystal or an electronic oscillator. In a DDS system, frequency tuning is provided by a digital signal that modulates a phase accumulator. The modulated clock frequency is mixed or upconverted as required. The signal is then amplified and applied to the on-chip antenna. Care must be taken to reduce on-chip capacitance in order to ensure a good coupling of the code to the on-chip antenna. A folded antenna will be required to fit the antenna on the chip. To keep antenna size small, the system should operate in the 1–50 gigahertz range. In this embodiment, the host is equipped with an optical spectrum analyzer for determination and identification of the spectral transparent code.

The Terminal Apparatus

Figure 18:
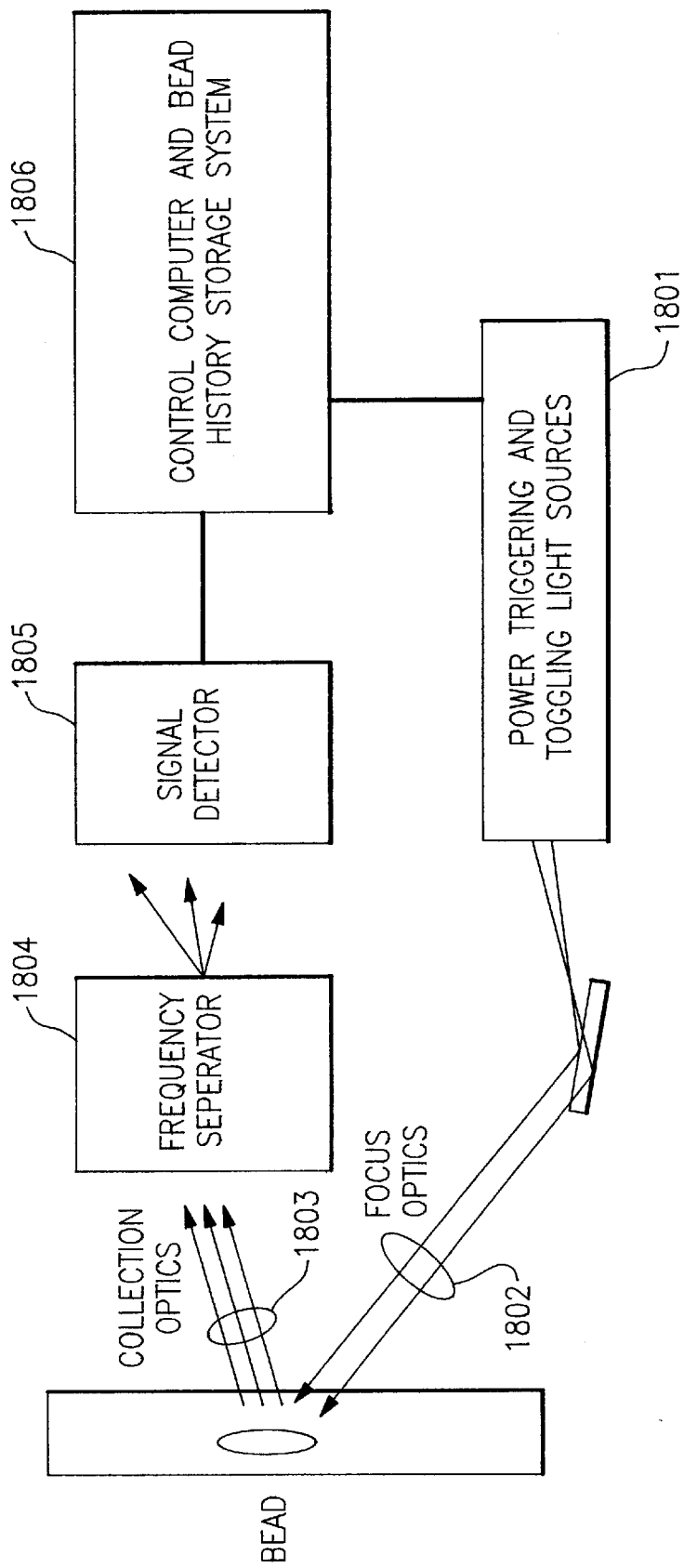
FIG. 18 is a simplified top view of the terminal apparatus.

The terminal apparatus is an integral part of the invention. Referring to FIG. 18, the terminal apparatus includes an optical power source 1801 to enable bead frequency code emission, focusing optics 1802 to apply power to the bead, bead signal collecting means 1803, electromagnetic frequency separation means 1804, an exemplar of which is a spectrometer, signal detection means 1805, an exemplar of which is a detector array, and a computer control system 1806 to decode and store ID tag spectral code information, as well as the sequence of chemical reaction steps associated with each bead. An embodiment of a terminal apparatus used for permutation encoding will also include a communications interface that functions to provide toggling signals to clock out the sequence of spectral emissions.

The optical power source 1801 may comprise any light source that is able to generate light with an intensity and wavelength that is adequate to provide operating power to the on-bead tag spectrum emitter during an operating read. Examples of such light sources include arc lamps, lasers, etc. Lasers used to power SMLs, DFLs, photoluminescent microcavity emitters, and Raman emitting microspheres. Lasers are in general pulsed Q switched lasers that emit 1–10 nsec pulses in the 530–650 nm range. Lasers used to power electroluminescent devices and permutation coding systems emit continuous wave pulses at 750–1000 nm. Similarly, the power absorbing devices of the beads preferably comprise any photoelectric device that is able to receive light from the host and generate therefrom sufficient energy to operate the ID tag for at least one operating cycle. Examples of such devices include photovoltaic cells that include a metal-semiconductor contact. Silicon or, more generally any material that is compatible with semiconductor wafer fabrication, may be used for this purpose.

The power supplying focusing optics 1802 of the terminal apparatus incorporates standard optical elements required to deliver optical energy to a 2 mm diameter bead. These elements comprise lens, fresnel zone plates, and mirrors. The bead emitted electromagnetic spectral code collecting means includes similar optics as well as incorporating integrating spheres and fiber optics.

The bead signal collecting means 1803 means includes lenses, mirrors, and integrating spheres. The electromagnetic frequency separation means 1804 includes the grating, prism, and accousto-optic spectrometers, as well as, color and interference filter arrays. The dispersed spectrum is recorded on one or two dimensional photodiode or charge coupled device arrays as the signal detection means 1805. For emitted electromagnetic spectrums that include wavelength bands below 1 micron, silicon detectors are used. Above 1 micron wavelength bands, GaAs detectors or other III-V detector materials are used in an appropriate conventional manner.

The communication interface of the terminal apparatus for permutation encoding includes a light transmitting device, which may be a laser or light emitting diode (LED), for emitting optical signals toward the on-bead tag or microchip. It also includes a light receiving device which comprises photodiodes, photodiode arrays or photomultiplier tubes, for receiving optical signals from the on-bead electromagnetic radiation sources. These optical signals are encoded as patterns of single wavelength light pulses or multi-wavelength code in a combination permutation-combination encoded tag. If multifrequency combination coding is used, a spectrometer is interposed between the bead and the photodetectors, to separate the frequency coded spectral components for independent recording on an array of photon detectors. The photons used by these interfaces are preferably in the visible to near visible part of the electromagnetic spectrum.

The computer control system 1806 includes conventional stored programs, data storage devices, analog to digital converters, digital to analog converters, and central processing units to allow smooth functioning of the entire system.

The Combinatorial Chemistry Synthetic Process

Figure 19:
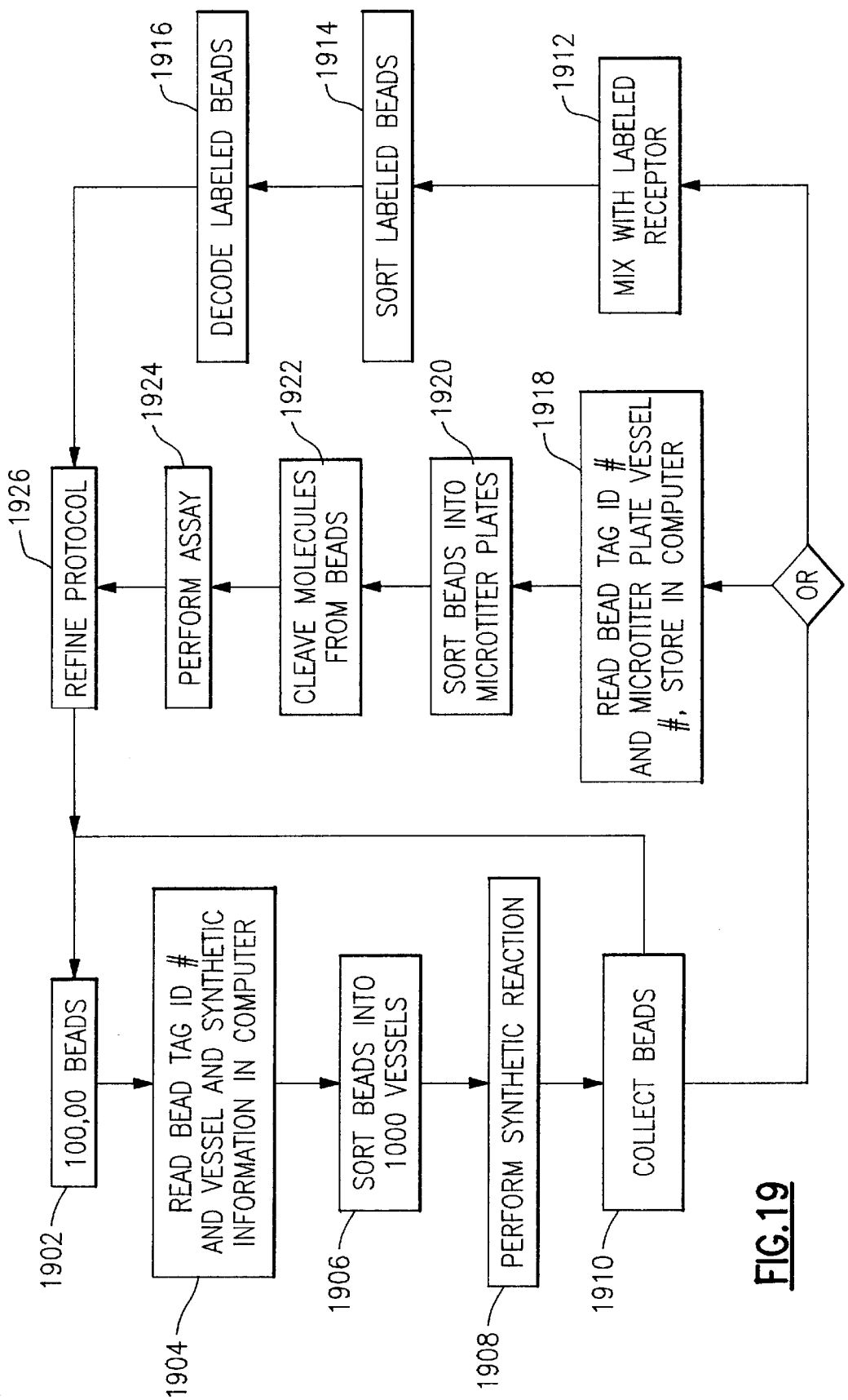
FIG. 19 is a flow chart that illustrates an exemplary protocol of a sequences of steps of a combinatorial synthesis system of the type with which the apparatus of the invention may be used, in this case a synthesis system compatible with polypeptides.

Referring now to FIG. 19, The utility of the present invention is well illustrated. In use, an operator selects an adequate number of beads 1902.

In a flow stream before the beads enter into the vessels, or are sorted, the ID tags of the beads are powered-by the terminal apparatus light source either by radiating the electromagnetic spectrum emitter itself with a resultant natural emission of frequency shifted radiation, or by radiating an absorbing medium such as a photoelectric cell that converts the energy of the light source into an electric potential and current to power the electromagnetic spectrum emitter. In response to this powering, the ID tags of the beads are caused to emit their distinct spectral code which is received and read 1904 by the terminal apparatus. The light source can be a laser, arc lamp, or similar device, dependent upon the specific type of electromagnetic spectrum emitter, that produces light of an intensity sufficient to penetrate the vessel and/or the medium in which the beads are contained, as discussed in greater detail in the Terminal Apparatus description of this patent. It is understood that the process of transmission and receival in the terminal apparatus will be complementary to the mode of transmission and receival of power and information utilized by the ID tag of the bead. The distinct ID tag spectral code is transmitted to the terminal apparatus and decoded and identified by the terminal apparatus, thus identifying the bead, and the bead ID number is stored in the terminal apparatus along with the particular vessel and synthetic reaction conditions that the bead is to be, or alternatively has been, or is being, subjected to.

The beads are then divided or sorted into a selected number of reaction vessels 1906. The number of utilized beads may vary depending upon various factors, including the size of the beads, the type of reactions being carried out, and the medium in which the reactions will be carried out. In addition, cost considerations may enter into the decision as to how many beads will be used in a particular study. The number of reaction vessels will depend upon the specific synthesis reactions being studied. For example, an operator investigating polypeptides for pharmaceutical applications might select twenty-two vessels, each vessel containing one of the twenty-two naturally occurring amino acids.

When the beads are introduced into the vessel, the oligomeric compounds attached to each bead may react with the selected reagents 1908 in the vessel to synthesize a new compound.

The beads are then collected 1910. At that point, the operator may repeat the procedure to continue to build a longer chain molecule, or the operator may decide that the compound is sufficiently synthesized in order to assay for possible reactivity with a target molecule, such as a pharmaceutical target. At that point, at least two possible reactivity test pathways may be chosen by the operator.

In the first, the operator may mix the beads with a labeled receptor 1912. For example, the receptor may be labeled with a fluorescent label. The novel molecules which bind with the target receptor molecule are sorted 1914 by any of the sorting methods known in the art. A possible sorting method might entail the tagged beads passing through a laser field which reads the florescent-labeled beads and passing through a single or series of deflection plates which perform the function of sorting the tagged beads.

After sorting, the ID tag information of each bead is read, decoded, and identified 1916 by the terminal apparatus via the methods described herein and in other sections of this patent. In this way, the molecule (oligomeric compound)that is bound to the target and the method of synthesizing that molecule are determined by correlating successful molecular binding with ID tag spectral code and the synthetic reaction history of each bead stored within the terminal apparatus by the methods described herein. In this way, the specific compound and synthesis reaction leading thereto can be determined by the information that has been transferred to and recorded by the terminal apparatus. This information can be analyzed and used to refine the protocol on subsequent uses of the beads 1926.

Alternatively the ID tag information of each bead may be read, decoded, and identified 1918 by the terminal apparatus via the methods described herein, and sorted into individual microtiter plate vessels 1920. Here one or more beads may be placed in each microtiter vessel. Prior to deposition into each vessel the bead ID spectral code is read by the methods described herein and stored in the terminal apparatus, along with the microtiter plate and storage vessel ID identifiers. After deposition, the synthesized compounds are cleaved from the beads 1922 by photochemical or chemical means well known to those skilled in the state of the art. Removed compounds are then used for chemical binding assays or biological functional assays 1924 to select for molecules of the appropriate functionality. Successful assay results are then correlated in the terminal apparatus with bead ID tag spectral code and bead synthetic history. The new round of combinatorial synthesis may then take place to refine molecular structure 1926.

Figure 20:
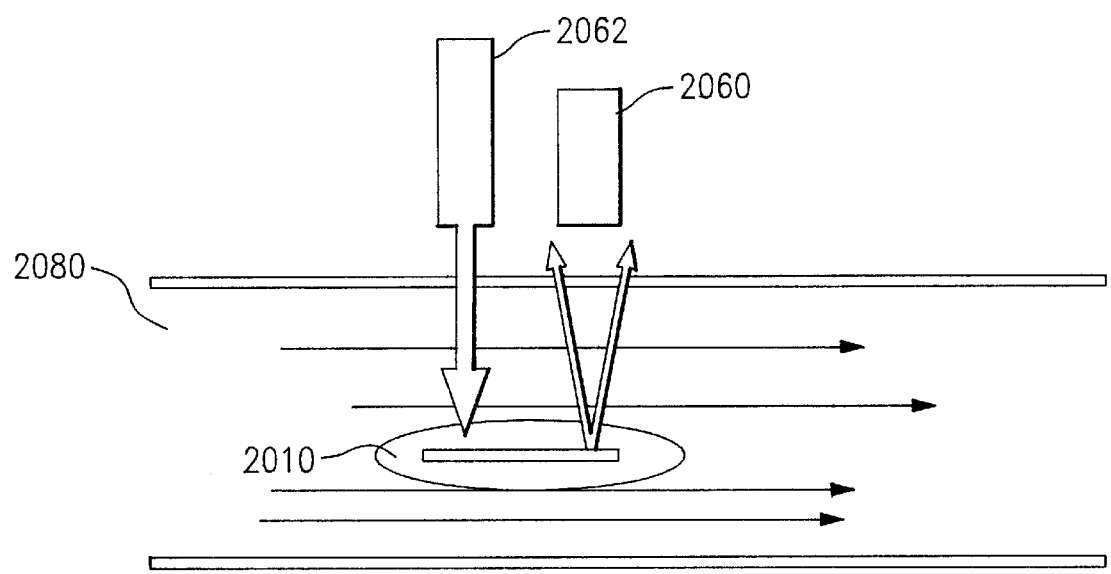
FIG. 20 is a greatly enlarged, simplified side view of a bead guide channel of a type that may be used to power up and read the bead of the invention.

Referring now to FIG. 20, it may be desirable to sort the beads 2010 and transport the beads into and through a tube 2080 which is shaped to bias the beads 2010 into a configuration that is most advantageous to receive and transmit information. For example, the bead 2010 and tube 2080 may be shaped to bias the bead 2010 so that if the ID tag is fabricated on a planar substrate the plane of the ID tag aligns with the terminal apparatus and the light-source 2062, thereby facilitating rapid and efficient transfer of information and power.

Referring again to FIG. 19, because the beads may be surrounded with the growth matrix, it is possible and desirable to wash the beads with an agent that will release the products of synthesis attached thereto so that the beads may be reused 1920. The wash step can be carried out by the appropriate chemical agent, that being a chemical agent which will strip the molecule from the anchoring site while not degrading the encapsulate material. Alternatively, the growth matrix may be attached to a portion of the ID tag, without an encapsulation. In this embodiment the growth matrix may be attachable or washable. Attachment is accomplished by chemical or mechanical means. Detachment and attachment is used to alter growth matrix material or provide fresh matrix for a new round of synthesis.

While the present invention has been described with reference to a number of specific embodiments, it will be understood that the true spirit and scope of the present invention should be determined with reference to the appended claims.

What is claimed is:

1. Improved synthesis beads for use in combinatorial synthesis processes that includes at least one bead sorting step, wherein said beads include;

(a.) a region on which is disposed a growth matrix, (b.) a molecular anchoring site attached to said growth matrix and (c.) a photoemissive region;

wherein the improvement comprises a plurality of vertical cavity surface emitting lasers in said photoemissive region for radiating electromagnetic radiation over each of a plurality of different predetermined wavelength bands, said wavelength bands being sufficiently narrow to allow said wavelength bands to be distinguished from one another when said lasers are emitting radiation simultaneously, whereby the application of electromagnetic radiation to said beads sufficient to stimulate simultaneous lasing activity in said surface emitting lasers, when used in connection with at least one bead sorting step, causes said surface emitting lasers to emit a predetermined combination of wavelength bands that allows a bead to be distinguished from a plurality of other beads that emit electromagnetic radiation at different combinations of wavelength bands.

2. A bead as set forth in claim 1 in which said bead further includes scattering means for scattering the electromagnetic radiation emitted by the lasers thereof.

3. A bead as set forth in claim 1 in which the widths of said wavelength bands are at most approximately 50 nm.

4. A bead as set forth in claim 1 further including photoelectric means for receiving electromagnetic radiation applied to said beads and generating from the latter radiation to a voltage sufficient to stimulate lasing activity in the lasers of said bead.

5. A bead as set forth in claim 1 in which the electromagnetic radiation applied to said bead during said at least one sorting step, and the electromagnetic radiation emitted by said lasers all have wavelengths that are included in the band of wavelengths that extends from the near infrared to the near ultraviolet of the electromagnetic spectrum.

6. The apparatus of claim 1 further including a terminal apparatus that includes radiation emitting means for successively applying, to each of a plurality of said beads, electromagnetic radiation sufficient to stimulate lasing activity in the lasers thereof, radiation detecting means for successively detecting the electromagnetic radiation emitted by the lasers of said beads, and identifying means responsive to said detecting means for distinguishing said beads from one another on the basis of the combinations of wavelength bands emitted by the lasers thereof.

7. An improved apparatus for use in combinatorial chemistry including:
 (a.) a terminal apparatus including;
  (i.) radiation emitting means for applying electromagnetic radiation to a plurality of mobile transport beads,
  (ii.) radiation detecting means for detecting electromagnetic radiation emitted by said beads and
  (iii.) identifying means responsive to said detecting means for distinguishing said beads based on the wavelength bands of the electromagnetic radiation emitted thereby;
 (b.) mobile transport beads, each bead including;
  (i.) a region on which is disposed a growth matrix,
  (ii.) a molecular anchoring site attached to said growth matrix and
  (iii.) a photoemissive region;
wherein the improvement comprises a plurality of vertical cavity surface emitting lasers in said photoemissive region for radiating electromagnetic radiation over each of a plurality of different predetermined wavelength bands, said wavelength bands being sufficiently narrow to allow said wavelength bands to be distinguished from one another when said lasers are emitting radiation simultaneously, whereby the application of electromagnetic radiation to said beads sufficient to stimulate simultaneous lasing activity in said surface emitting lasers, when used in connection with at least one bead sorting step, causes said surface emitting lasers to emit a predetermined combination of wavelength bands that allows a bead to be distinguished from a plurality of other beads that emit electromagnetic radiation at different combinations of wavelength bands.

8. An apparatus as set forth in claim 7 in which the wavelengths at which said stimulating electromagnetic radiation is emitted do not include wavelengths that fall within said plurality of predetermined different respective wavelength bands.

9. An apparatus as set forth in claim 7 in which said beads further include scattering means for scattering the electromagnetic radiation emitted by the lasers thereof, whereby said radiation detecting means may detect the electromagnetic radiation emitted by the lasers of said beads without regard to the orientation of said beads with respect to said terminal apparatus.

10. An apparatus as set forth in claim 7 in which the widths of said wavelength bands are at most approximately 50 nm.

11. An apparatus as set forth in claim 7 in which each of said beads further includes photoelectric means for receiving said stimulating electromagnetic radiation and for generating therefrom a voltage sufficient to stimulate lasing activity in the lasers of that bead.

12. An apparatus as set forth in claim 7 in which the electromagnetic radiation emitted by the lasers of said beads all have wavelengths that extend from the near infrared to the near ultraviolet of the electromagnetic spectrum.

* * * * *